(12) United States Patent
Banaszak-Holl et al.

(10) Patent No.: US 8,568,692 B2
(45) Date of Patent: Oct. 29, 2013

(54) METHOD FOR ANALYZING COLLAGENOUS TISSUES FOR THE DETECTION AND DIAGNOSIS OF BONE DISEASE

(75) Inventors: Mark Banaszak-Holl, Ann Arbor, MI (US); Joseph Wallace, Indianapolis, IN (US); Blake Erickson, Ann Arbor, MI (US); Clifford M. Les, Birmingham, MI (US); Bradford G. Orr, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 388 days.

(21) Appl. No.: 12/847,408

(22) Filed: Jul. 30, 2010

(65) Prior Publication Data

US 2011/0189716 A1 Aug. 4, 2011

Related U.S. Application Data

(60) Provisional application No. 61/273,192, filed on Jul. 31, 2009.

(51) Int. Cl.
*A61K 49/00* (2006.01)

(52) U.S. Cl.
USPC .......................................................... 424/9.1

(58) Field of Classification Search
None
See application file for complete search history.

(56) References Cited

U.S. PATENT DOCUMENTS

2011/0189716 A1 * 8/2011 Banaszak-Holl et al. ...... 435/29

OTHER PUBLICATIONS

Wallace, J. et al., "Nanoscale morphology of Type I collagen is altered in the Brtl mouse modle of Osteogenesis Imperfecta", J. Struct. Biol., 2011, vol. 173: pp. 146-152.*

* cited by examiner

*Primary Examiner* — Michael Burkhart
(74) *Attorney, Agent, or Firm* — Harness, Dickey & Pierce, P.L.C.

(57) ABSTRACT

Methods and systems for diagnosing a bone disease related to collagen pathology in a subject are provided. These include providing a bone sample from the subject and determining a quantitative collagen morphology value of the bone sample. A reference value is provided from a non-affected control subject where the reference value is a quantitative collagen morphology value from the same type of bone sample obtained from a population of non-affected control subjects. The quantitative collagen morphology value of the subject's bone sample is compared to the reference value. If the collagen morphology value is altered versus the reference value, the subject is diagnosed as having a collagen related bone disease. The collagen morphology value can include mean fibril spacings and distributions of the fibril spacings taken from a subject's bone sample.

Figure 1:
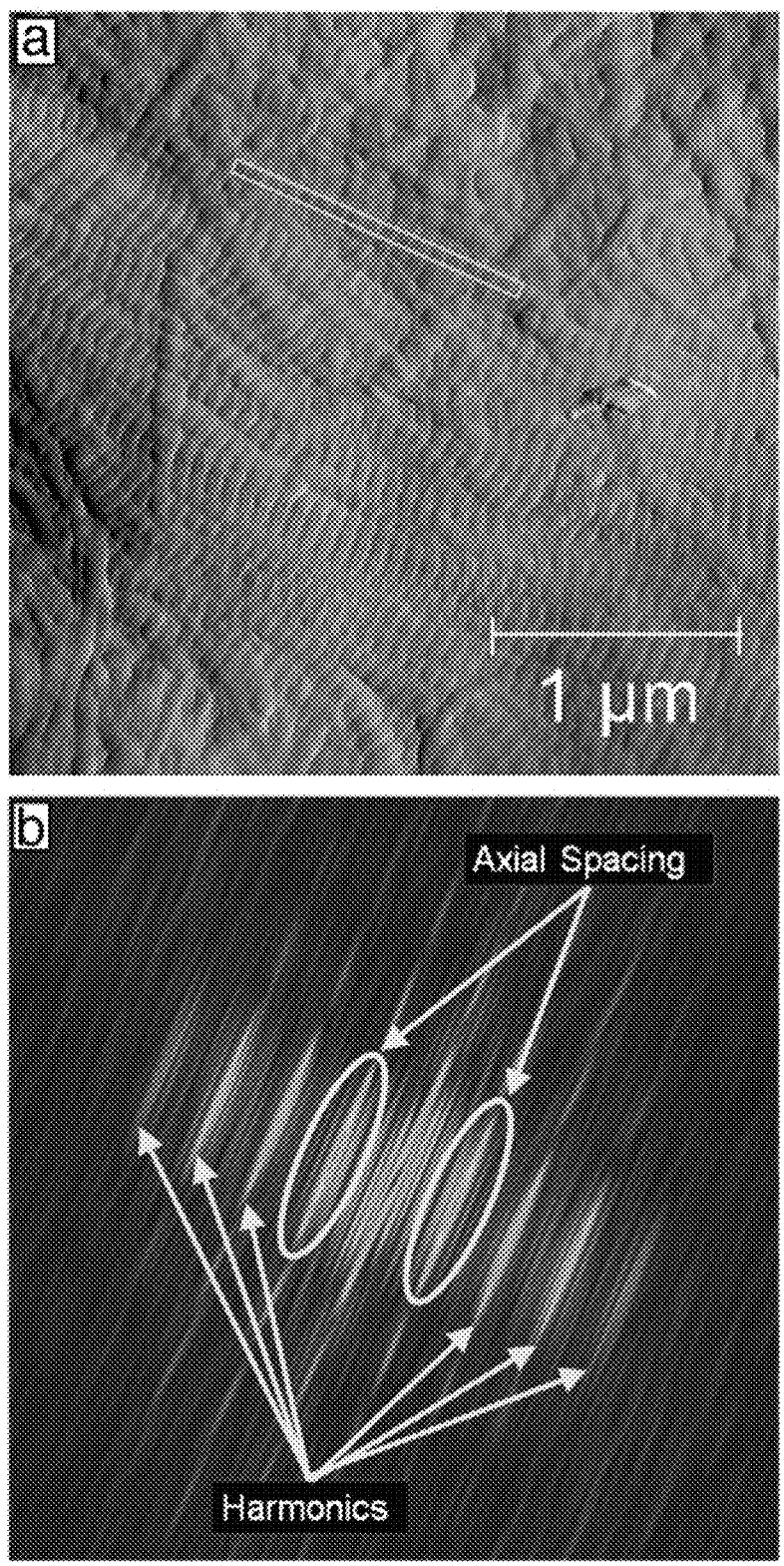

18 Claims, 20 Drawing Sheets
(16 of 20 Drawing Sheet(s) Filed in Color)

METHOD FOR ANALYZING COLLAGENOUS TISSUES FOR THE DETECTION AND DIAGNOSIS OF BONE DISEASE

CROSS-REFERENCE TO RELATED APPLICATIONS

This application claims the benefit of U.S. Provisional Application No. 61/273,192, filed on Jul. 31, 2009. The entire disclosure of the above application is incorporated herein by reference.

GOVERNMENT RIGHTS

This invention was made under Grant number DE018840 awarded by the National Institutes of Health. The government has certain rights in the invention.

FIELD

The present disclosure relates to detecting and diagnosing bone diseases relating to collagen structure, including osteoporosis and osteogenesis imperfecta in a subject using type I collagen morphology.

INTRODUCTION

This section provides background information related to the present disclosure, which is not necessarily prior art.

Bone is an exquisitely evolved biological material with a complex hierarchical structure. At its most fundamental level, bone is a two-phase composite composed of a relatively soft and ductile collagen matrix that is impregnated with and surrounded by a much stiffer, stronger reinforcing carbonated apatite phase. Despite the importance of bone health to overall health, there is a lack of knowledge regarding the ultrastructure of bone and how mineral and collagen, and their interaction with one another, relate to clinically-relevant tissue-level and structural-level properties. Disease, nutrition, trauma and mechanical loads can impact bone at multiple levels of the tissue hierarchy, including the tissue ultrastructure.

Although many diseases affect bone through changes in mineral and the organic matrix, osteoporosis is the most common bone disease and is a major medical and economic burden facing society. Each year, an estimated 1.5 million Americans suffer an osteoporotic fracture resulting in direct-care expenditures of 18 billion dollars a year and often leading to a downward spiral in quality of life or even death. An estimated 10 million Americans over the age of 50 have osteoporosis, and another 34 million are considered at risk. On a more global scale, 75 million people in the US, Europe and Japan combined have osteoporosis, and as many as 9 million osteoporotic fractures were reported worldwide in the year 2000. A combination of the aging population coupled with a lack of knowledge concerning the material mechanism of the disease and less than ideal diagnostic tools means that the number of osteoporotic hip fractures in the United States could triple by the year 2040.

Clinically, osteoporosis is defined in a person as having a bone mineral density (BMD) that is 2.5 standard deviations below the peak bone mass of the average healthy person of the same gender, as measured by dual-energy x-ray absorptiometry (DEXA). Although popular and widely used, DEXA has several limitations. Most significantly, standard DEXA uses a two-dimensional (2D) projection to measure areal BMD ($g/cm^2$) versus true volumetric BMD ($g/cm^3$). This 2D measurement is, therefore, dependent on the size and shape of the measured bone and can underestimate true BMD. Regardless of the method used to measure BMD, estimating fracture risk based solely on BMD is not sufficient. Normal BMD does not guarantee protection from osteoporotic fracture, and many cases of osteoporosis do not become clinically evident until fracture occurs. Current diagnostic methods for osteoporosis focus exclusively on bone quantity and mineral content and fail to take into account the important biological role of collagen matrices.

Another significant bone disease is osteogenesis imperfecta which is believed to be caused by genetic defects that affect the body's ability to make strong bones. In dominant (classical) osteogenesis imperfecta, a person has too little type I collagen or a poor quality of type I collagen due to a mutation in one of the type I collagen genes. In recessive osteogenesis imperfecta, mutations in other genes interfere with collagen production. The result in all cases is fragile bones that break easily.

It is often, though not always, possible to diagnose osteogenesis imperfecta based solely on clinical features. Clinical geneticists can also perform biochemical (collagen) or molecular (DNA) tests that can help confirm a diagnosis of osteogenesis imperfecta in some situations. These tests generally require several weeks before results are known. Both the collagen biopsy test and DNA test are thought to detect almost 90% of all type I collagen mutations. A positive type I collagen study confirms the diagnosis of dominant osteogenesis imperfecta, but a negative result could mean that either a collagen type I mutation is present but was not detected or the patient has a form of the disorder that is not associated with type 1 collagen mutations or the patient has a recessive form of osteogenesis imperfecta. Therefore, a negative type I collagen study does not rule out osteogenesis imperfecta. When a type I collagen mutation is not found, other DNA tests to check for recessive forms are needed and thus prolong confirmatory diagnosis and increase the time taken for proper diagnosis and screening.

It is, therefore, important to develop quantitative methods to assess the ultrastructure in bone and other tissues. Such methods could facilitate the diagnosis of bone disease and could identify the underlying mechanism of the disease in order to better focus treatment and intervention.

SUMMARY

This section provides a general summary of the disclosure and is not a comprehensive disclosure of its full scope or all of its features.

Methods are provided for identifying a subject as a disease candidate where the disease affects tissue comprising collagen. A sample of tissue comprising collagen, such as dentin, bone, tendon, or skin, is provided from the subject. A collagen fibril morphology value is determined for the tissue sample. A reference value, being a reference collagen fibril morphology value determined using a tissue sample from a control subject, is provided where the tissue sample from the control subject is the same type of tissue as the tissue sample from the subject. For example, determining a collagen fibril morphology value of the tissue sample can include imaging the tissue using atomic force microscopy and measuring D-periodic gap/overlap spacing of a collagen fibril or a plurality of collagen fibrils. Also, the reference value can include a D-periodic gap/overlap spacing of a collagen fibril or a plurality of collagen fibrils from the control subject. The collagen fibril morphology value of the tissue sample is then compared to the reference value. The subject is identified as a disease candidate when the collagen fibril morphology value is different from the reference value. Such methods can use bone tissue to identify a subject as an osteoporosis candidate or an osteogenesis imperfecta candidate.

Further areas of applicability will become apparent from the description provided herein. The description and specific examples in this summary are intended for purposes of illustration only and are not intended to limit the scope of the present disclosure.

DRAWINGS

The patent or application file contains at least one drawing executed in color. Copies of this patent or patent application publication with color drawing(s) will be provided by the Office upon request and payment of the necessary fee. The drawings described herein are for illustrative purposes only of selected embodiments and not all possible implementations, and are not intended to limit the scope of the present disclosure.

FIG. 1. Schematic of two-dimensional fast Fourier transform measurements in mineralized bone. Panel a shows a representative 3.5 μm×3.5 μm amplitude (error) image that was used to measure the collagen fibril axial D-periodicity. The yellow box represents a fibril that was chosen for measurement. Panel b shows the corresponding 2D FFT from this fibril. As indicated, the 2D spectrum contains information about the harmonic characteristics of the fibril. The circled peaks are the first harmonic in the spectrum. The maximum value in this peak corresponds to the axial repeat distance of the fibril (in this case, 68 nm).

Figure 2:
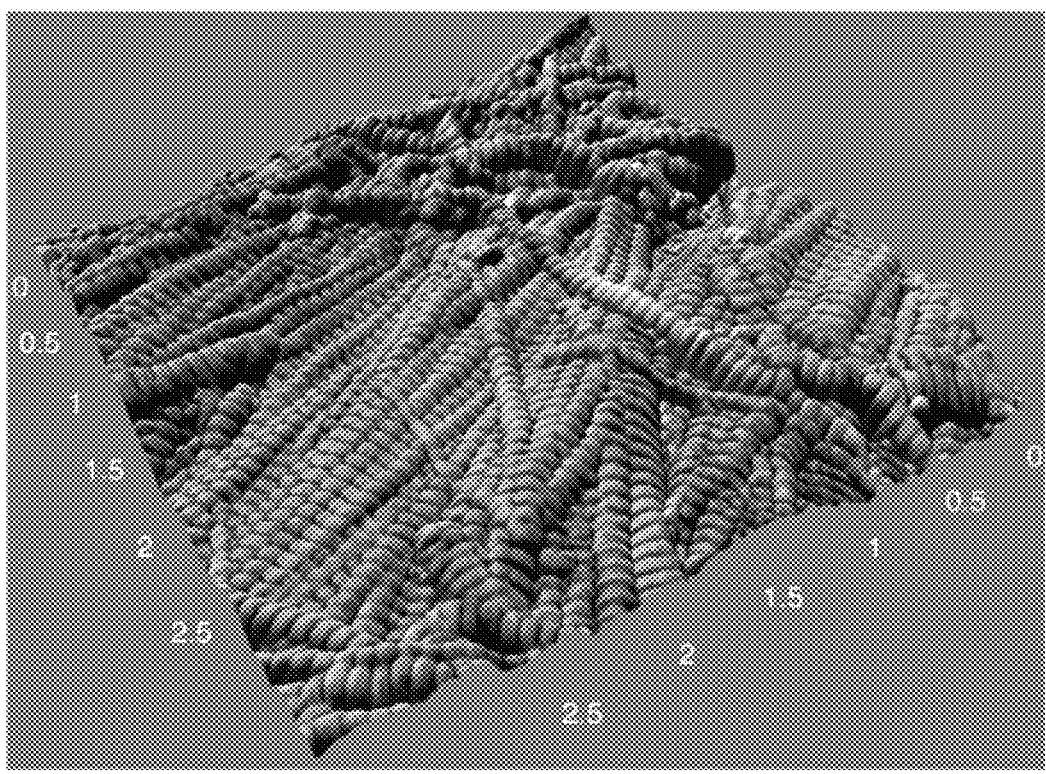

FIG. 2. Three-dimensional rendering of an intracortical region in the murine femur. To produce this figure, a phase image was used as a texture overlay on the corresponding topography (height) image to produce a rendering of the surface. In this representative 3.5 μm×3.5 μm image (150 nm height), the rich sample topography characteristic of bone is evident. A bundle of collagen fibrils is seen spanning the surface immediately adjacent to disorganized, woven collagen.

Figure 3:
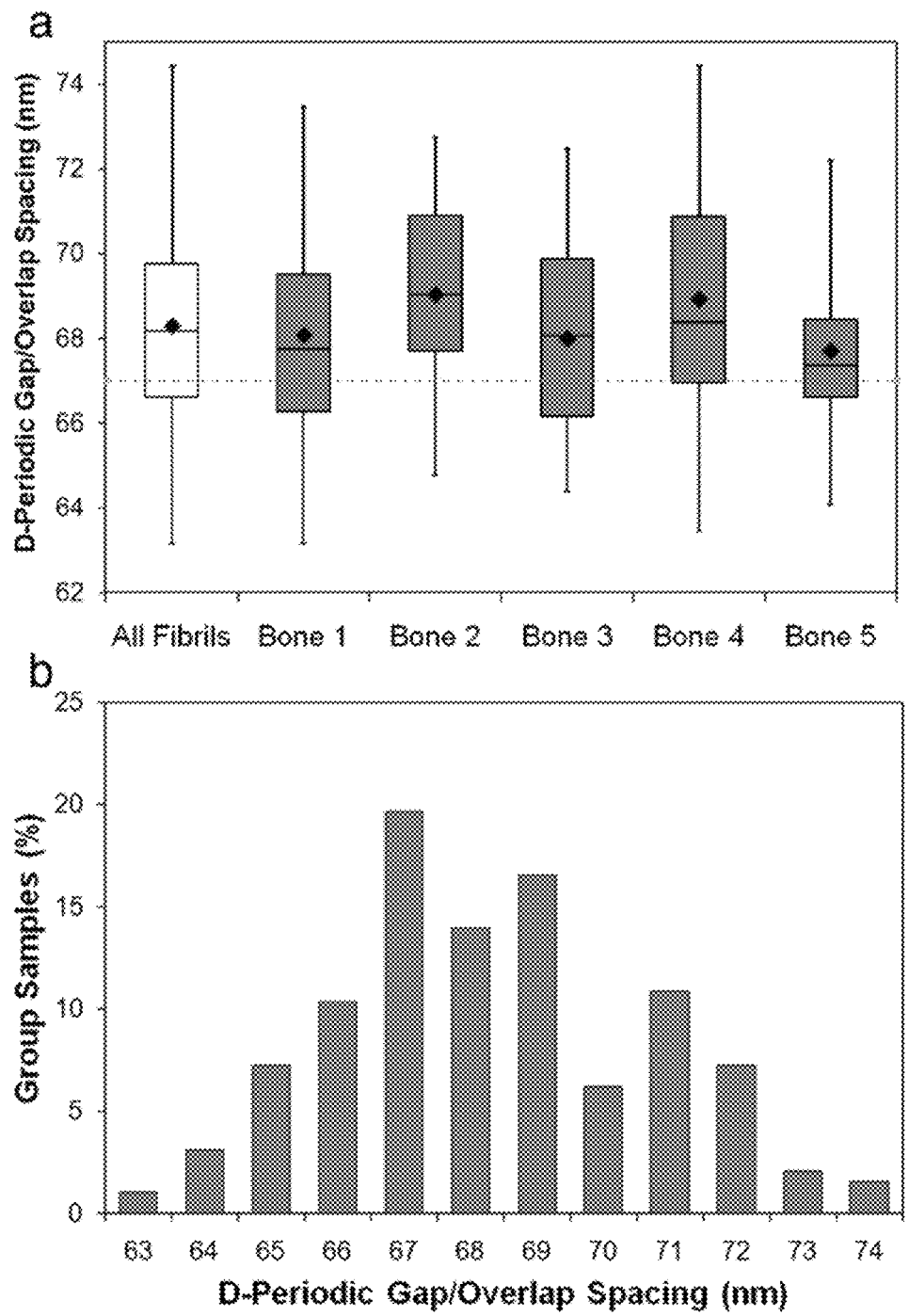

FIG. 3. Axial D-periodic gap/overlap spacings from murine femora. Panel a shows the boxplot representation of the axial gap/overlap spacing from each of the 5 femurs measured, as well as from all fibrils combined. The dashed horizontal line indicates the expected 67 nm repeat distance. For each sample, the box is the interquartile region (middle 50% of the data), the horizontal line inside of the box is the median, and the diamond is the mean. The whiskers on the box are the minimum and maximum observation in each group. When the axial gap/overlap spacings from all 193 fibrils are viewed as a histogram with a 1 nm bin size in panel b, there is a population of fibrils near the theoretical 67 nm value. However, the spacing of the fibrils has a distribution ranging from near 63 nm to 74 nm. This type of distribution is often overlooked, but may have important implications to the development of the anisotropic mechanical behavior of the bone tissue.

Figure 4:
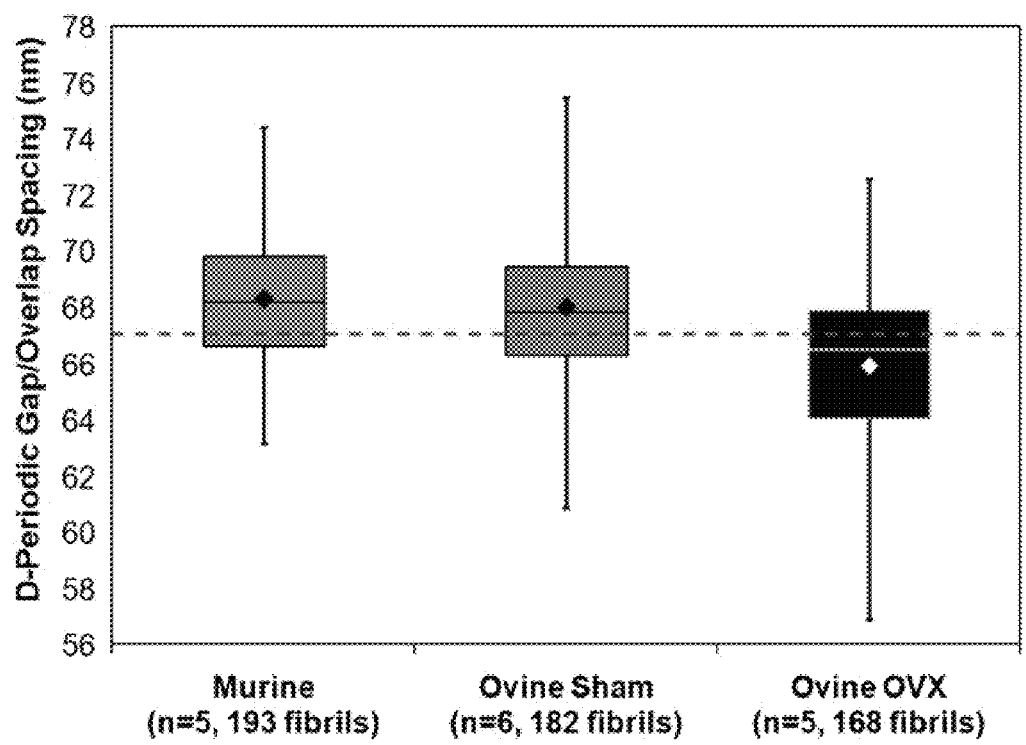

FIG. 4. Axial D-periodic gap/overlap spacings from murine femora and ovine radii. This figure shows the boxplot representation of the axial gap/overlap spacing from mouse, sham operated sheep and ovariectomized (OVX) sheep. The dashed horizontal line indicates the theoretical 67 nm repeat distance. When the sham samples were compared to OVX by one-way ANOVA, there was a significant difference present ($p=0.048$).

Figure 5:
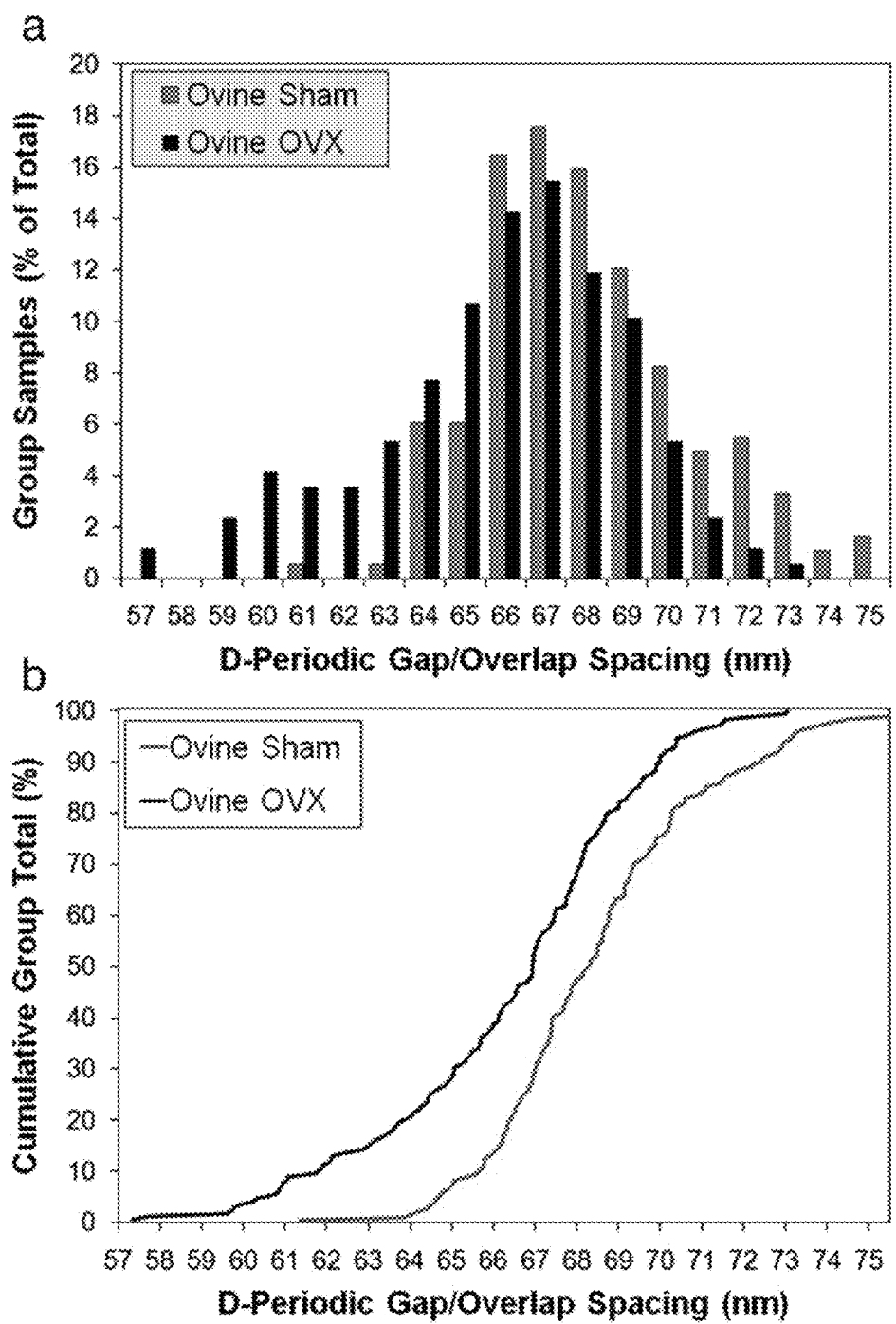

FIG. 5. Axial D-periodic gap/overlap spacings from ovine radii. Panel a shows the histogram representation of the axial gap/overlap spacing from sham operated sheep and ovariectomized (OVX) sheep. When the axial gap/overlap spacings from all fibrils are viewed as histograms with a 1 nm bin size, there is a population of fibril spacings in the OVX sheep at 64 nm or below that is almost completely absent from the Sham sheep. Panel b displays the Cumulative Density Function (CDF) calculated from each population. The CDF shows what fraction of a given sample is contained up to a particular value. A Kolmogorov-Smirnov (K-S) test performed on the two groups indicates that there is a significant difference in the population distributions of the two groups ($p<0.001$).

Figure 6:
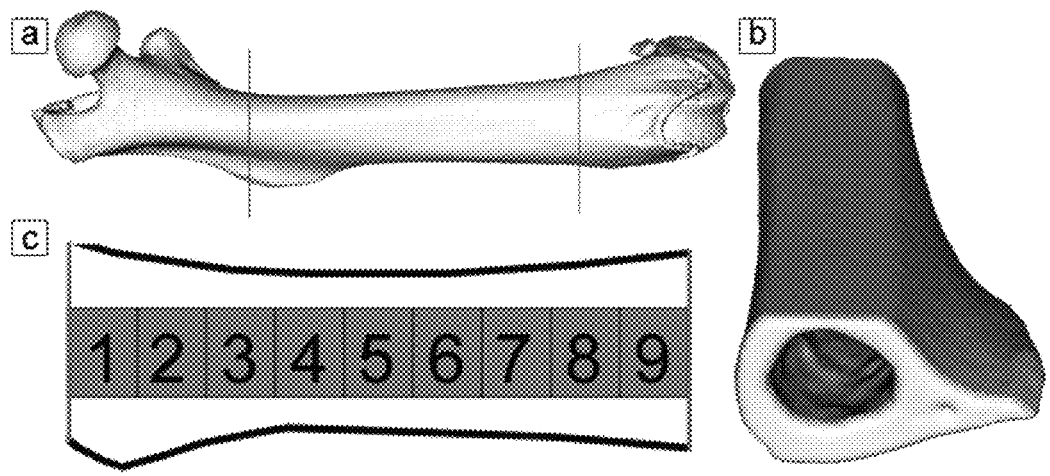

FIG. 6. Schematic representation of the processed mouse femur. Panel a shows a 3D image of a mouse femur, with the anterior surface of the femur facing the reader (proximal end left, distal end right). The femur was polished to create a flat intracortical region to image (panel b). Along the length of the femur, 9 locations were analyzed to investigate the collagen fibril ultrastructure (panel c).

Figure 7:
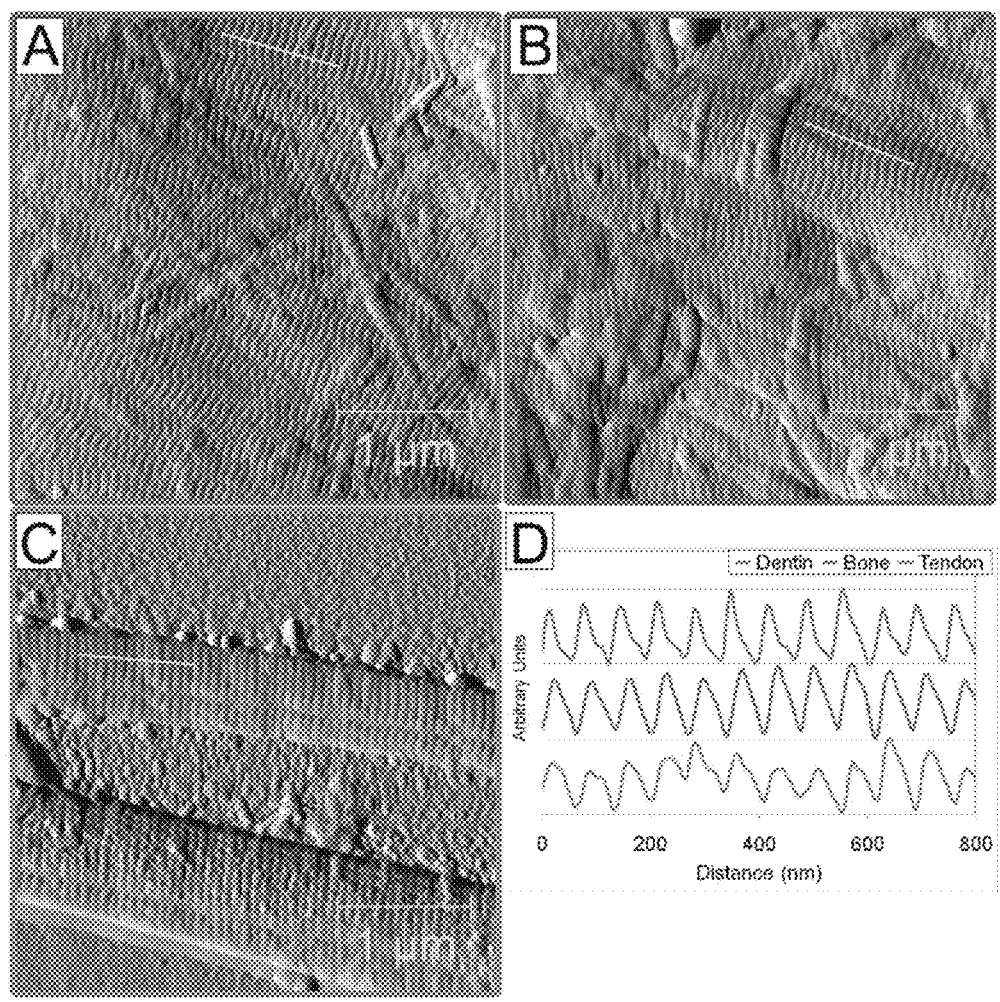

FIG. 7. Representative line scans from each tissue. This figure shows representative 3.5 μm×3.5 μm amplitude images from dentin (A) and bone (B), and a deflection image from tendon (C). The yellow line in each panel is where a representative line scan was performed (as shown in panel D). The line scans in panel D are shown on a normalized height scale for comparison purposes.

Figure 8:
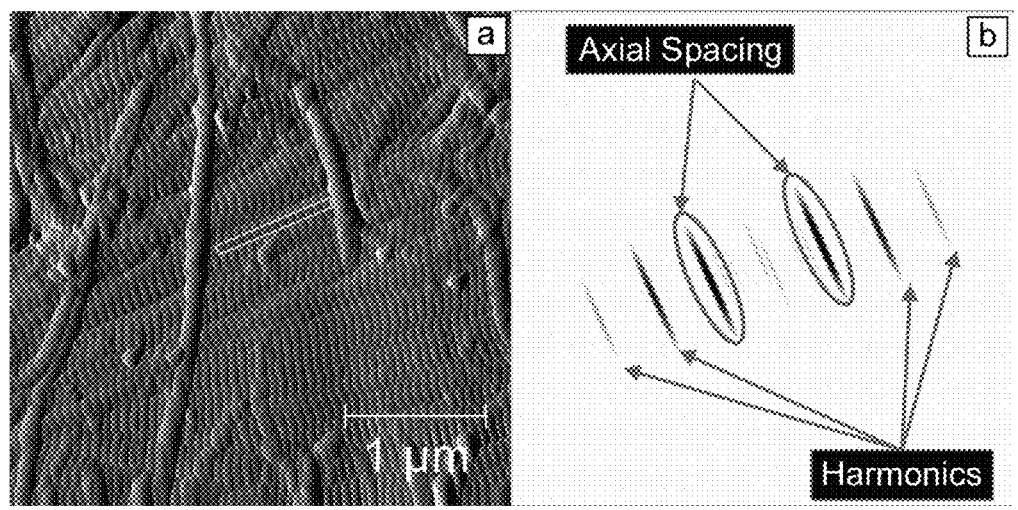

FIG. 8. Schematic representation of two dimensional fast Fourier transform measurements. Panel a shows a representative 3.5 μm×3.5 μm amplitude image from a bone sample that was used to measure the collagen fibril D-periodicity. The box represents a fibril that was chosen for measurement. Panel b shows the corresponding 2D FFT from this fibril. As indicated, the 2D power spectrum contains information about the harmonic characteristics of the fibril. The circled peaks are the first harmonic of the spectrum. The maximum value in this peak corresponds to the D-Periodic repeat distance of the fibril.

Figure 9:
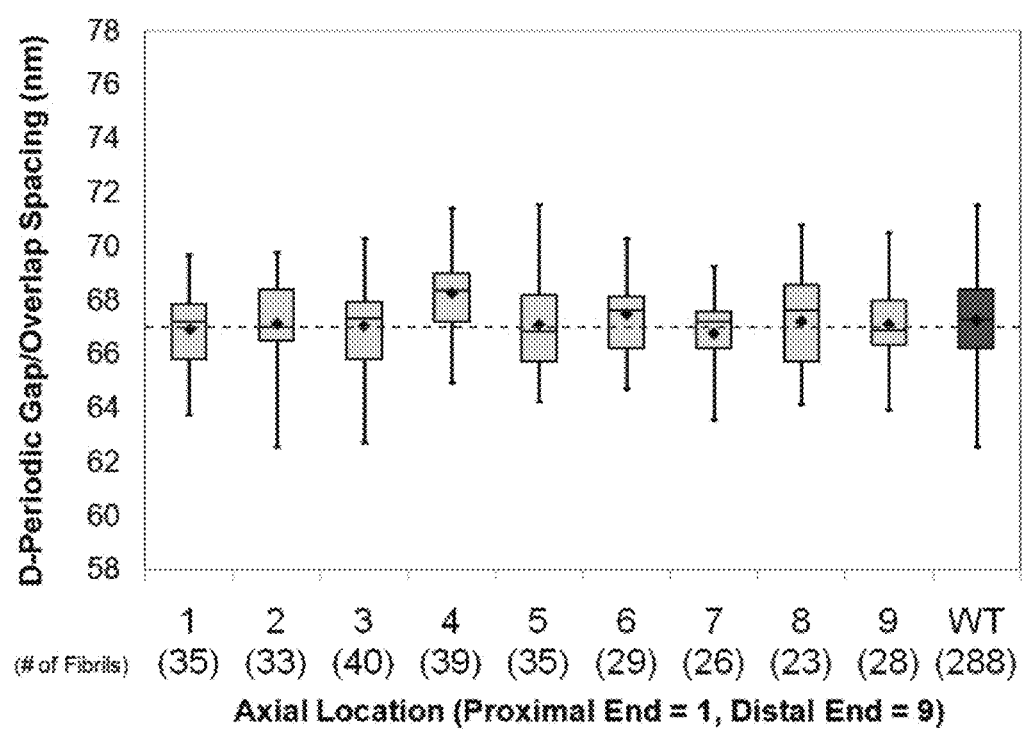

FIG. 9. D-periodic spacing as a function of axial location in bones. This figure shows the boxplot representation of the D-periodic spacing as a function of axial location in the bone samples. Data from the four bones were pooled at each location. This figure confirms that there were no systematic changes in collagen morphology as a function of location in the bone.

Figure 10:
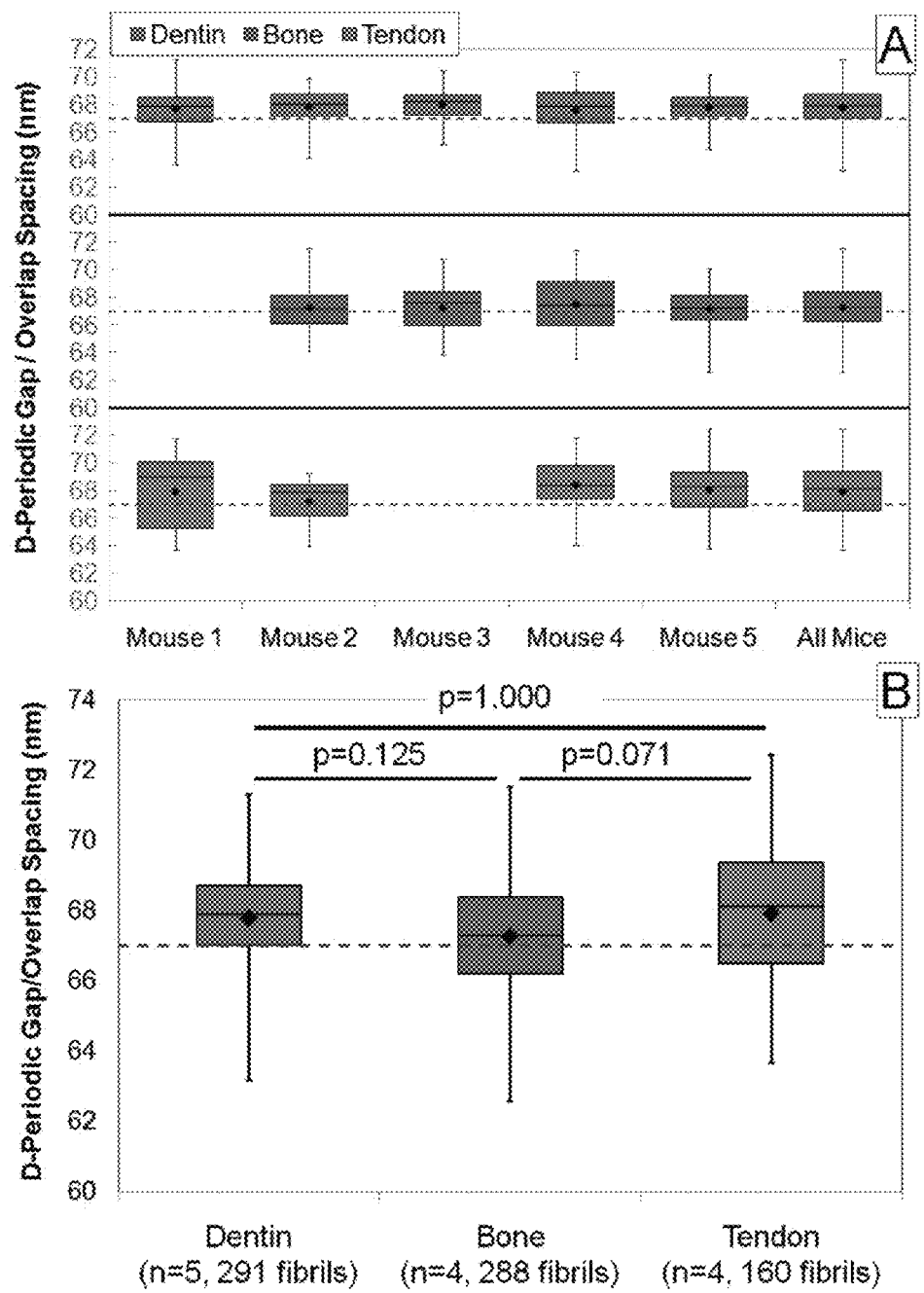

FIG. 10. D-periodic gap/overlap spacings from murine tissues. Panel A shows the boxplot representation from each sample in each tissue. The rightmost boxplot for each tissue in panel A is the boxplot for all measured fibrils within the tissue type. This boxplot is repeated in panel B. When the groups were compared by one way ANOVA with post hoc Bonferroni tests, there were no significant differences between any of the groups (p-values indicated for each comparison).

Figure 11:
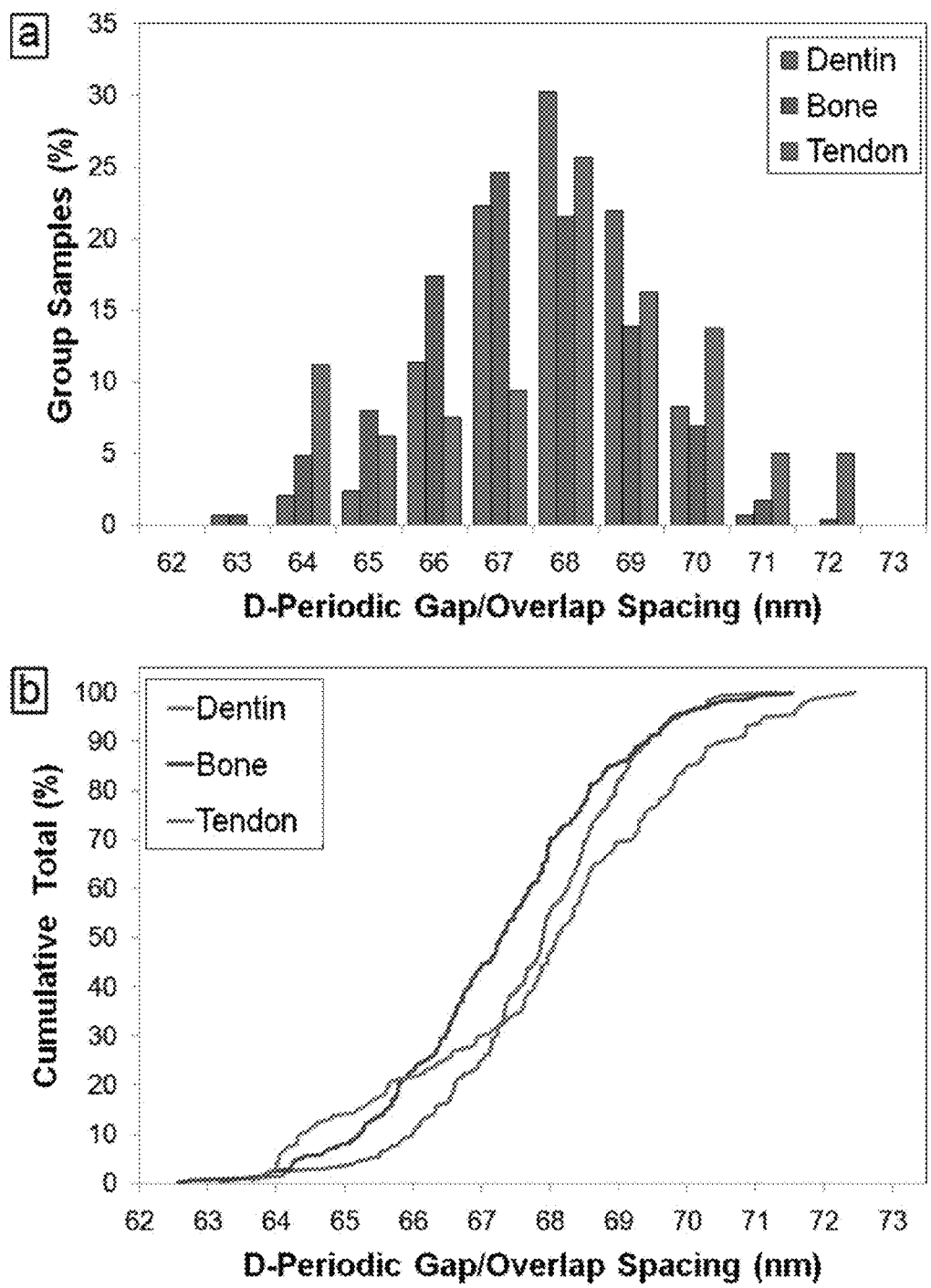

FIG. 11. Histogram and cumulative density function of D-periodic spacings from murine tissues. Panel a shows the histogram representation of the D-periodic gap/overlap spacing from dentin, bone, and tendon samples (1 nm bin size). Panel b displays the cumulative density function (CDF) calculated from each group. The CDF shows what fraction of a given sample is contained up to a particular value. A Kolmogorov-Smirnov test performed on the data indicates that there are significant differences in the population distributions between all the three groups.

Figure 12:
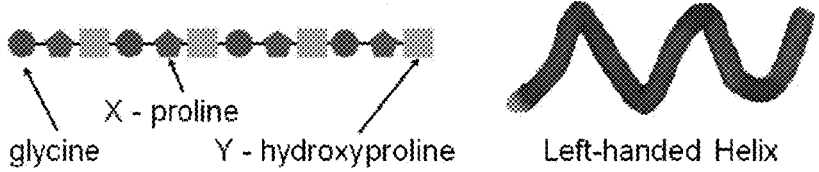
Figure 12:
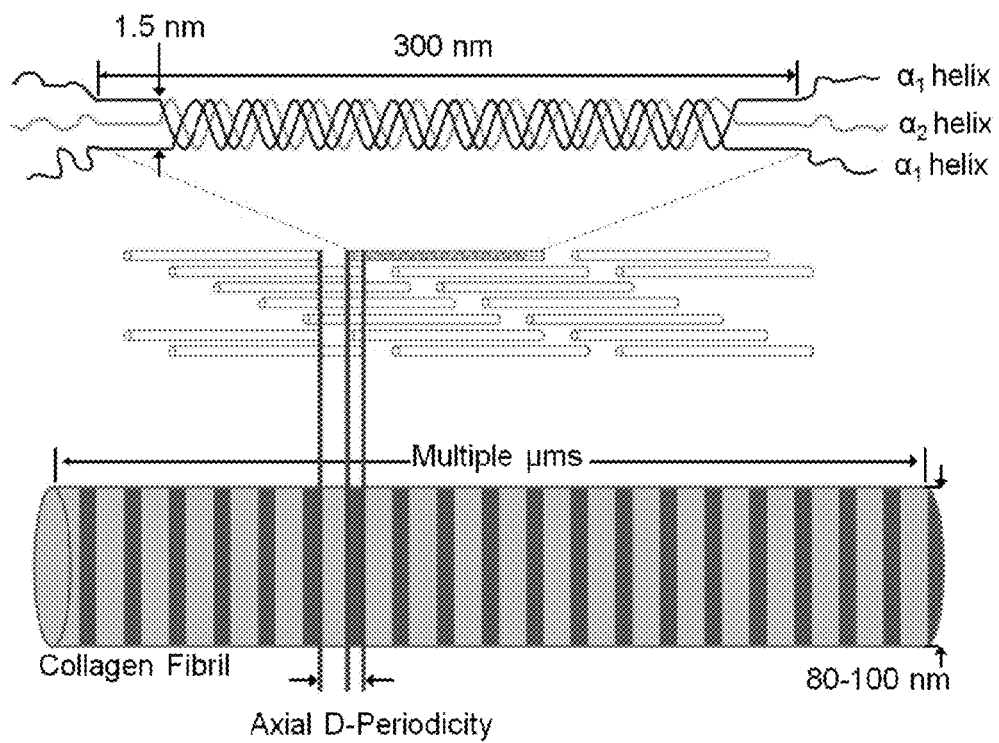
Figure 12:
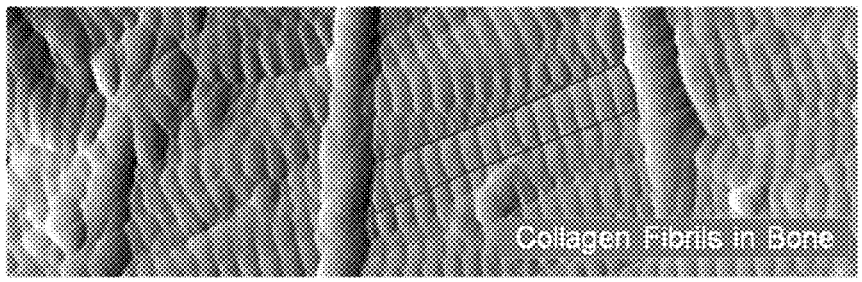

FIG. 12. Type I Collagen Fibrillar Organization. Collagen is first synthesized as a polypeptide chain of amino acids with uninterrupted regions including a repeating Gly-X-Y triplet (X and Y are often proline and hydroxyproline, respectively). This chain takes a left-handed helical conformation and then 3 chains come together to form a right-handed triple helix.

Once secreted from the cell, non-helical pro-peptide ends are enzymatically cleaved leaving a 300 nm long, 1.5 nm wide tropocollagen molecule. The molecules self-assemble in a staggered, parallel manner to form a 3D fibril. Because of the space between the ends of molecules and the offset from row to row, regions of gaps and overlaps exist within the fibril and produce an oscillating surface topography with a characteristic repeat pattern called the Axial D-periodicity.

Figure 13:
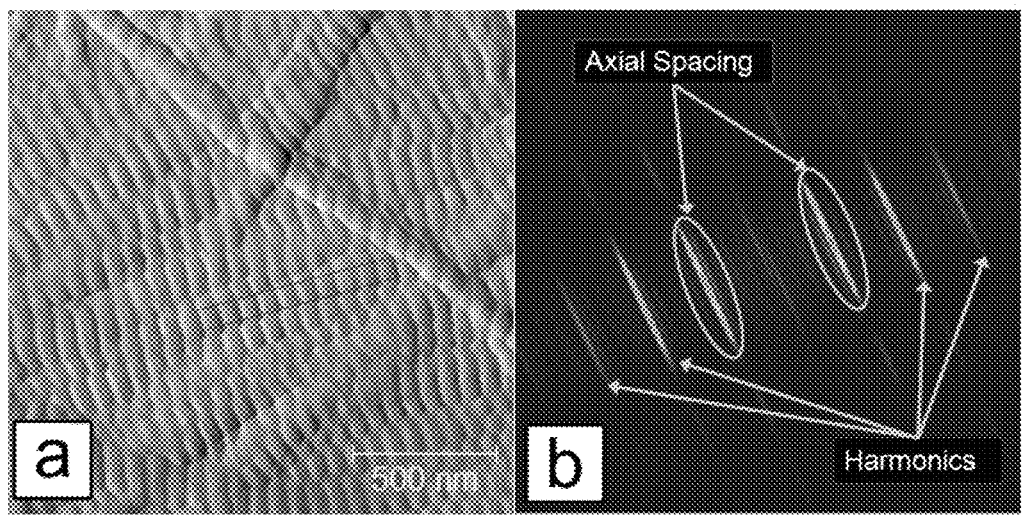

FIG. 13. Schematic Representation of Two Dimensional Fast Fourier Transform Measurements. Panel a shows a representative 3.5 µm×3.5 µm amplitude image that was used to measure the collagen fibril D-periodicity. The box represents a fibril that was chosen for measurement. Panel b shows the corresponding 2D FFT from this fibril. As indicated, the 2D power spectrum contains information about the harmonic characteristics of the fibril. The circled peaks are the first harmonic of the spectrum. The maximum value in this peak corresponds to the D-Periodic repeat distance of the fibril.

Figure 14:
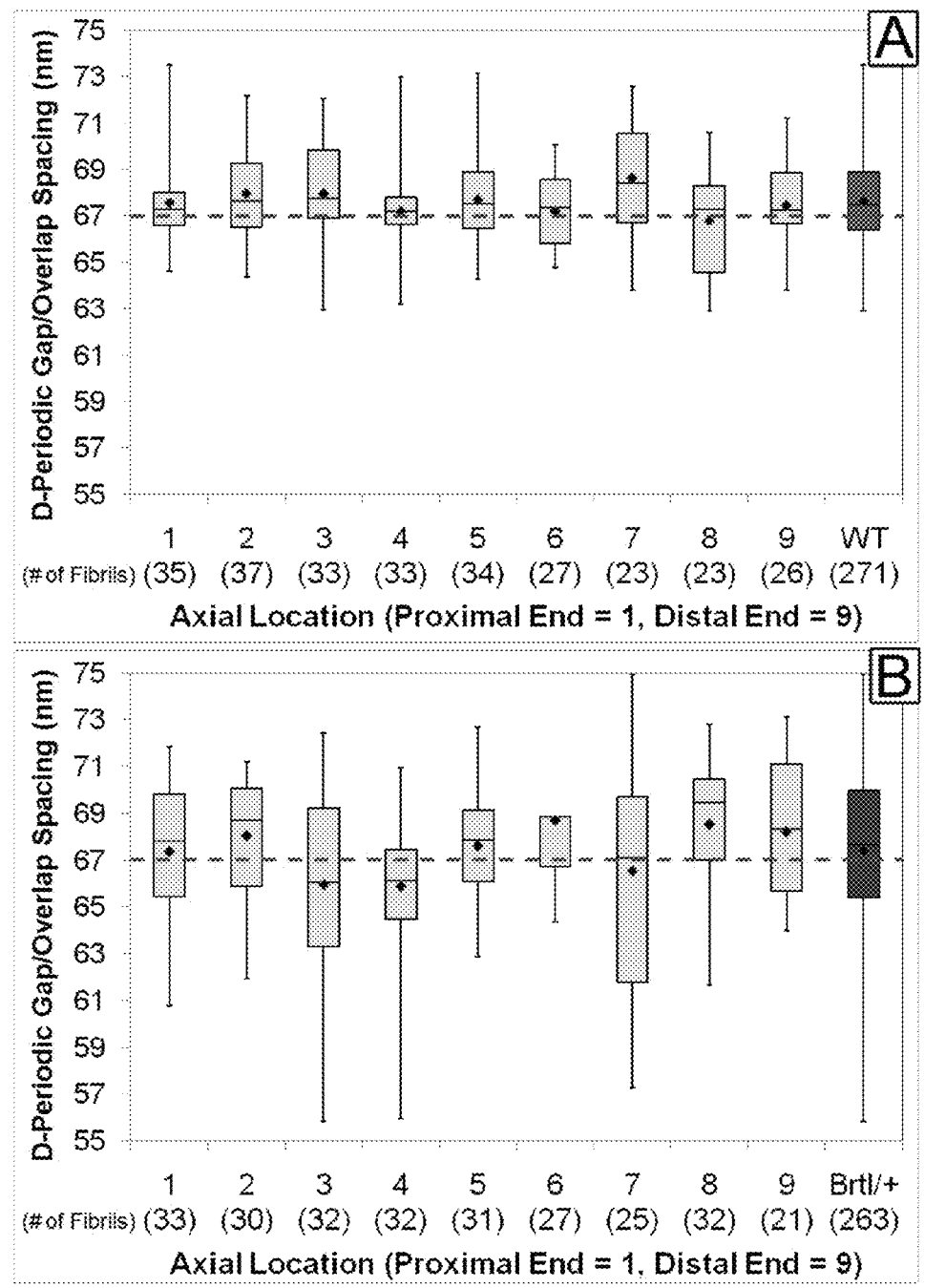

FIG. 14. D-Periodic Gap/Overlap Spacings from Murine Femora as a Function of Axial Location. This figure shows the boxplot representation of the axial gap/overlap spacing from WT (A) and Brt1/+ (B) bones as a function of axial location. The dashed horizontal line indicates the expected 67 nm repeat distance. For each sample, the box is the interquartile region (middle 50% of the data), the horizontal line inside of the box is the median, and the diamond is the mean. The whiskers on the box are the minimum and maximum observation for that location. Qualitatively, there is greater variability between axial locations in the Brt1/+ bones (B) in comparison to the WT (A) bones.

Figure 15:
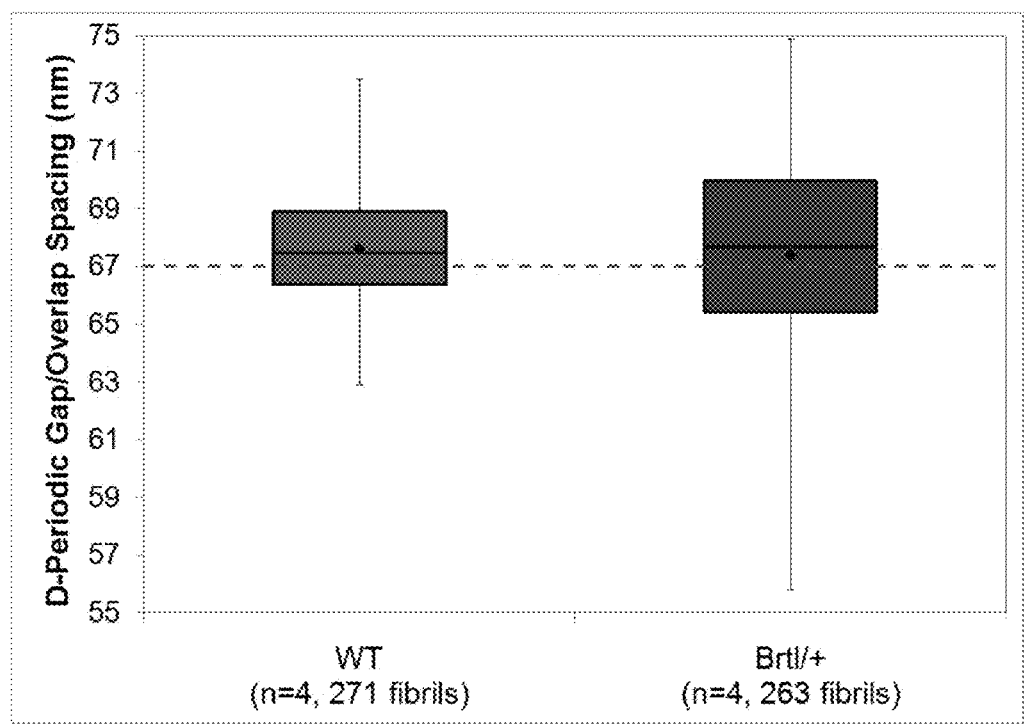

FIG. 15. D-Periodic Gap/Overlap Spacings from Murine Femora. Boxplot representation of the D-periodic gap/overlap spacing from the 4 bones in each genotype. The dashed horizontal line indicates the theoretical 67 nm repeat distance. When the mean values from the 4 samples in each group were compared by One Way ANOVA, WT and Brt1/+ mice (p=0.392) did not differ significantly.

Figure 16:
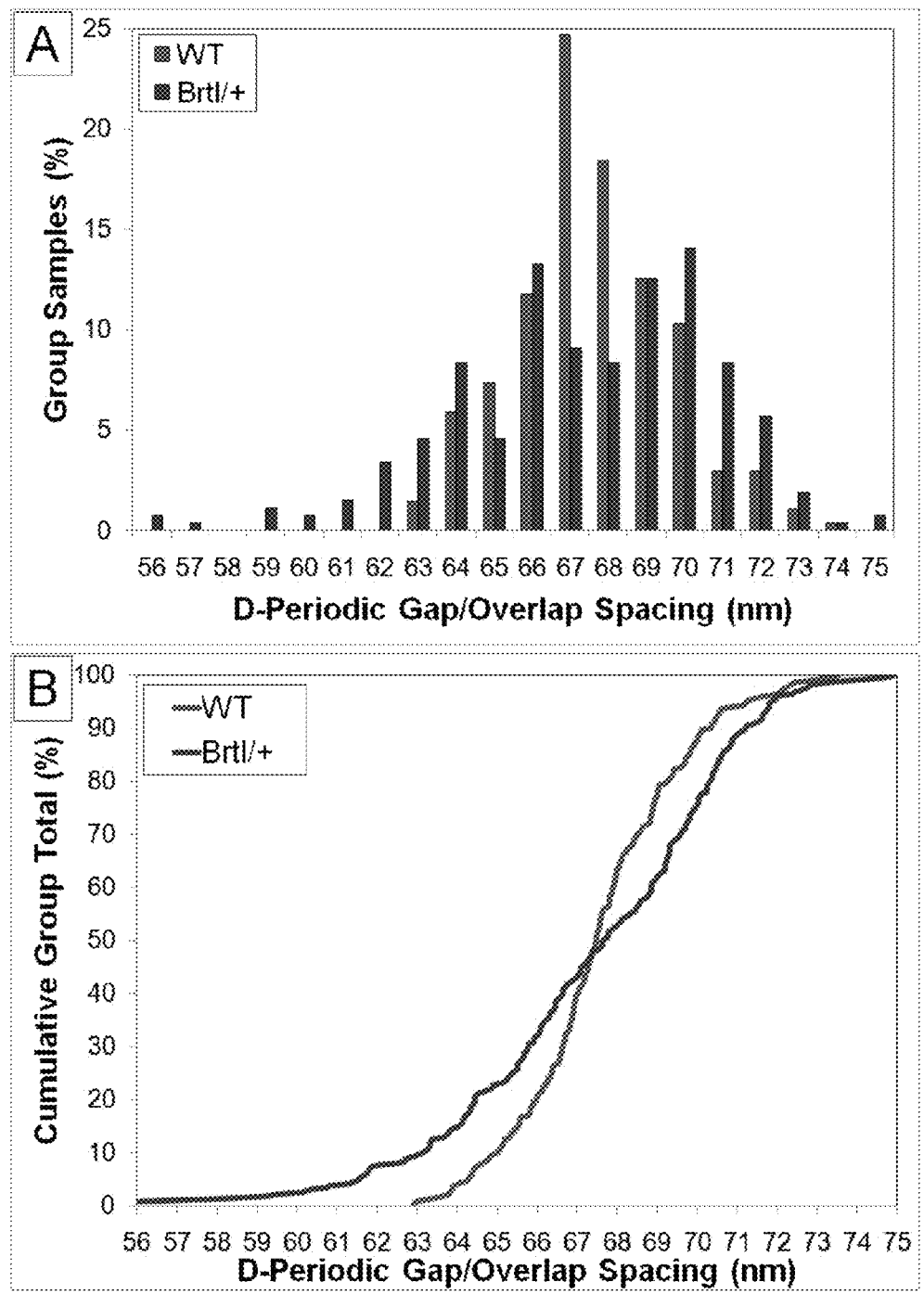

FIG. 16. Histogram and Cumulative Density Function of D-Periodic Spacings from Murine Bone. Panel A shows the histogram representation of the D-Periodic gap/overlap spacing from WT and Brt1/+ bones (1 nm bin size). Panel B displays the Cumulative Density Function (CDF) calculated from each group. The CDF shows the fraction of a given sample that is contained up to a particular value. A Kolmogorov-Smirnov test performed on the data distributions indicates that there is a significant differences in the population distributions between WT and Brt1/+ mice (p=0.001).

Figure 17:
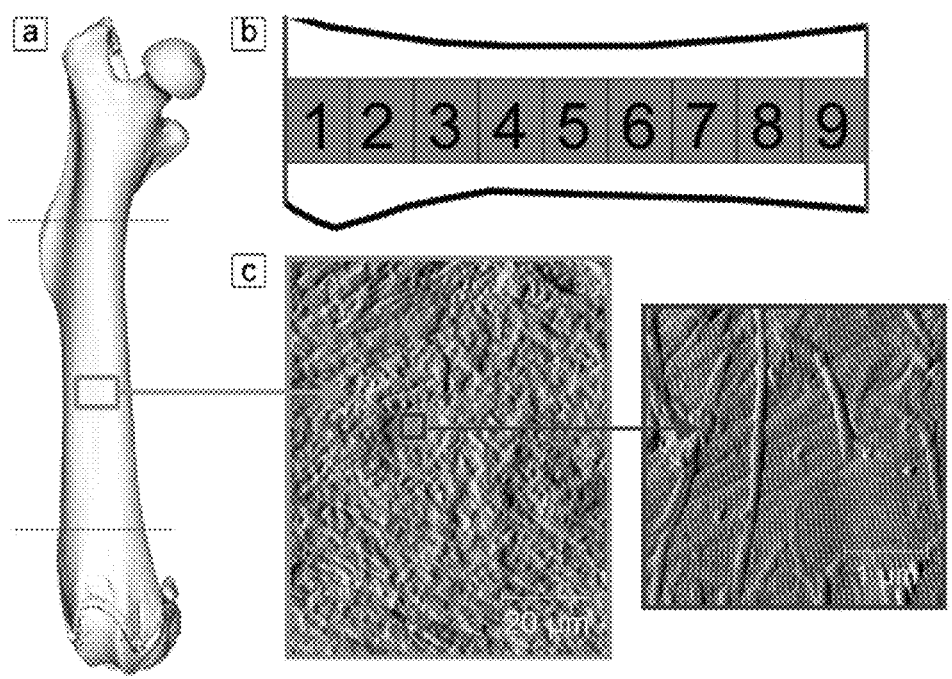

FIG. 17. Processing and Imaging of the Murine Femur. Panel a shows a 3D image of a mouse femur, with the anterior surface of the femur facing the reader. Nine locations along the length of each femur were analyzed to investigate the collagen fibril ultrastructure (panel b). Panel c shows a large scale image of the bone's surface, indicating a region of interest for closer investigation. At this location, a 3.5 µm×3.5 µm image was obtained and analyzed.

Figure 18:
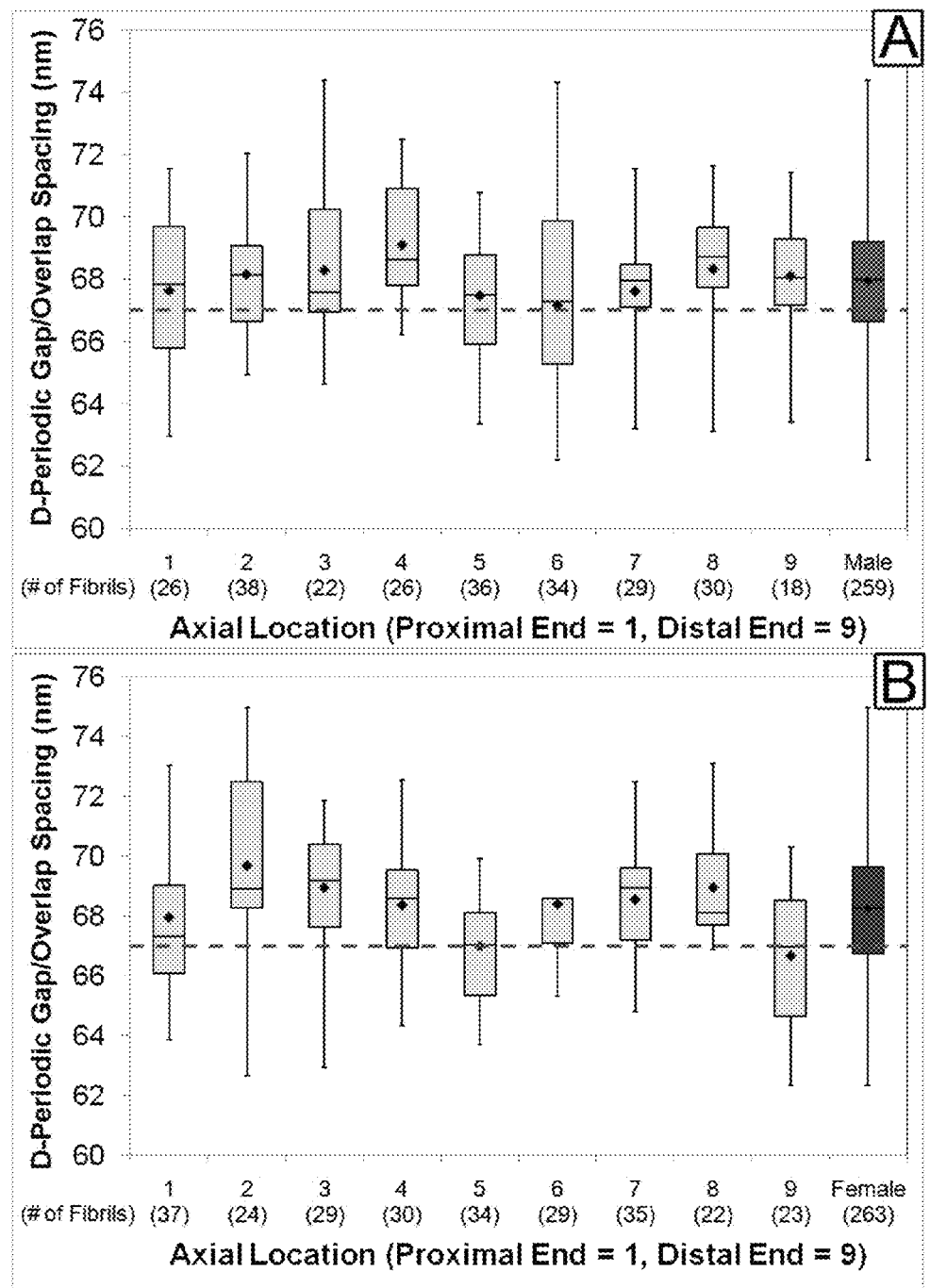

FIG. 18. D-Periodic Gap/Overlap Spacings from Male and Female Murine Femora as a Function of Axial Location. This figure shows the boxplot representation of the D-periodic gap/overlap spacing from Male (A) and Female (B) bones as a function of axial location. The dashed horizontal line indicates the expected 67 nm repeat distance. For each sample, the box is the interquartile region (middle 50% of the data), the horizontal line inside of the box is the median, and the diamond is the mean. The whiskers on the box are the minimum and maximum observation for that location. Although some statistical differences did exist between locations in each gender (Male: 4 vs. 6; Female: 2 vs. 9, 2 vs. 5, 8 vs. 9), there were no systematic differences in either gender.

Figure 19:
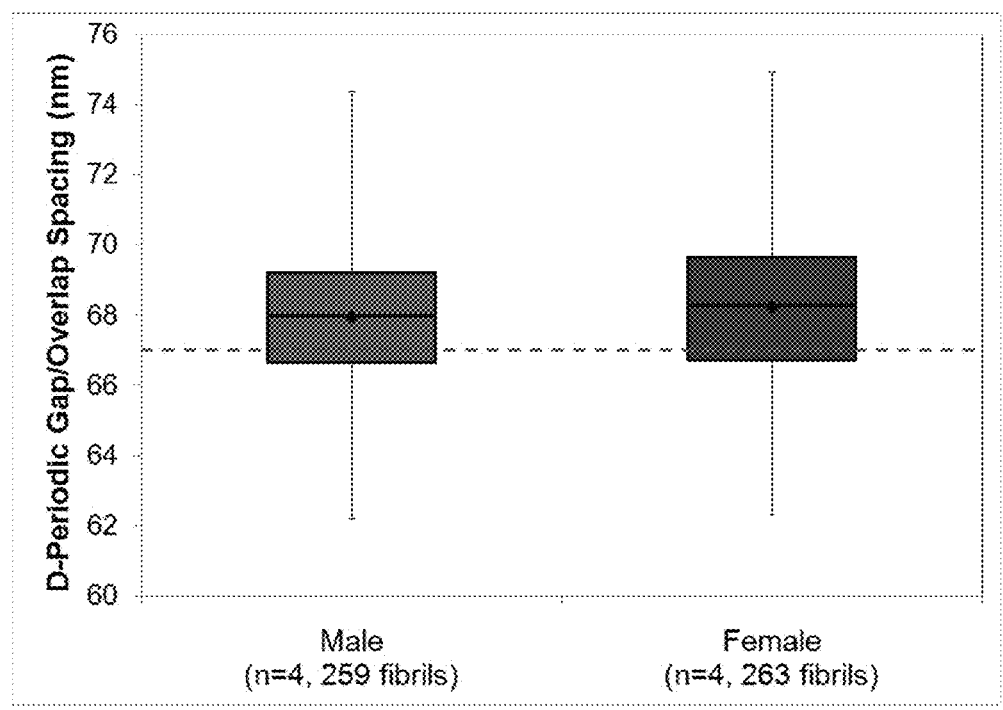

FIG. 19. Overall D-Periodic Gap/Overlap Spacings from Male and Female Murine Femora. This figure shows the boxplot representation of the D-periodic gap/overlap spacing from the 4 bones in each gender. The dashed horizontal line indicates the theoretical 67 nm repeat distance. When the mean values from the 4 samples in each group were compared by One Way ANOVA, male and female mice (p=0.564) did not differ significantly.

Figure 20:
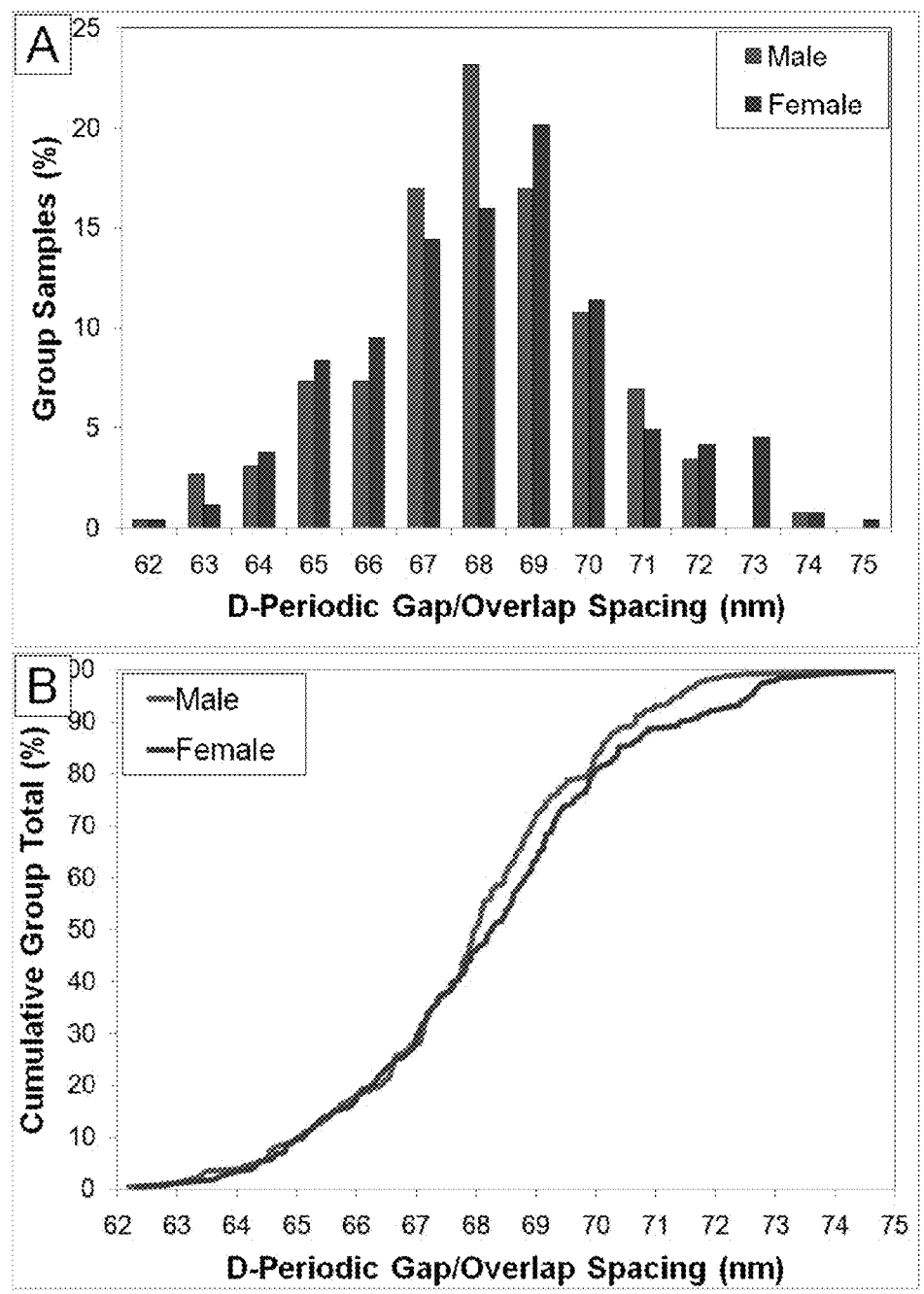

FIG. 20. Histogram and Cumulative Distribution Function of D-Periodic Spacings from Male and Female Murine Bone. Panel A shows the histogram representation of the D-Periodic gap/overlap spacing from Male and Female bones (1 nm bin size). Qualitatively, there were no differences present in the male and female population distributions. Panel B displays the Cumulative Distribution Function (CDF) calculated from each group. The CDF shows the fraction of a given sample that is contained up to a particular value. A Kolmogorov-Smirnov test performed on the data distributions indicates that there is a no detectable difference in the population distributions between Male and Female mice (p=0.276).

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

The present disclosure provides methods, systems, apparatus, and compositions relating to determining whether a subject has a bone disease, whether the subject is at risk for developing a bone disease, and for screening a subject to determine whether they have a bone disease, such as osteoporosis or osteogenesis imperfecta.

Bone evolved by nature to elegantly balance structural and metabolic needs in the body. Bone health is an integral part of overall health and an understanding of the ultrastructure of healthy bone can help identify how disease impacts the nanoscale properties of this biological material. The present technology demonstrates that quantitative assessments of a distribution of Type I collagen fibril morphologies can be made using atomic force microscopy (AFM). As identified herein, normal bone contains a distribution of collagen fibril morphologies and changes in this distribution can be directly related to disease state. Specifically, by monitoring changes in the collagen fibril distribution of sham-operated and estrogen-depleted sheep, the present technology demonstrates the ability to detect estrogen-deficiency-induced changes in Type I collagen in bone. This technology provides new insight into the ultrastructure of bone as a tissue and the role of material structure in bone disease. These observations afford a much-needed in vitro procedure that can complement current methods used to diagnose osteoporosis and other bone diseases.

Type I collagen is the most abundant protein in the body and forms the structural scaffolding upon which bone is built. The need for accurate quantitative analytical methods to assess collagen's nanoscale morphology and mechanical integrity with as little disruption to the tissue as possible prompted the present investigation of the collagen ultrastructure of bone using atomic force microscopy (AFM). Other methods successfully used to image the collagen ultrastructure of bone (e.g. transmission and scanning electron microscopy) require the removal of the sample from its natural surroundings followed by harsh preparation techniques including full dehydration and ultra-high vacuum, which may induce artifacts and ultimately reduce one's ability to draw accurate conclusions from the data. By way of comparison, AFM is a less-destructive high-resolution imaging modality which requires less sample preparation. Samples imaged using AFM can remain intact, implying that measured properties are characteristics of the sample and less likely artifacts of the processing or imaging. Other investigators have utilized AFM to image the collagen matrix in mineralized dentin and bone yielding high-resolution images. However, previous studies did not perform quantitative analyses of the bone ultrastructure to increase the understanding of the tissue morphology at this fundamental level of organization. By using AFM, the morphology of collagen fibrils in fully intact and mineralized bone can be imaged and quantitatively analyzed to learn more about the normal nanoscale properties of this material.

The present technology further demonstrates that collagen, the most abundant protein in animals, exists as a distribution of nanoscale morphologies in teeth, bones, and tendons. This fundamental characteristic of Type I collagen has not previously been reported and provides a new understanding of the nanoscale architecture of this ubiquitous and important biological nanomaterial. Dentin, bone, and tendon tissue samples were chosen for their differences in cellular origin and function, as well as to compare mineralized tissues with a tissue that lacks mineral in a normal physiological setting. A distribution of morphologies was present in all three tissues, confirming that this characteristic is fundamental to Type I collagen regardless of the presence of mineral, cellular origin of the collagen (osteoblast versus odontoblast versus fibroblast), anatomical location, or mechanical function of the tissue.

Bone also has a complex hierarchical structure that has evolved to serve structural and metabolic roles in the body. Due to the complexity of the bone structure and the number of diseases which affect the ultrastructural constituents of bone, it is important to develop quantitative methods to assess bone nanoscale properties in normal and disease states. For example, autosomal dominant osteogenesis imperfecta results predominantly from glycine substitutions (80%) and splice site mutations (20%) in the genes encoding the α1 or α2 chains of Type I collagen. Genotype-phenotype correlations using over 830 collagen mutations have revealed that lethal mutations are located in regions crucial for collagen-ligand binding in the matrix. However, these correlations have not been extended to collagen structure in bone.

The present technology uses an atomic force microscopy-based approach to image and quantitatively analyze the morphology of Type I collagen fibrils in femora from heterozygous (Brt1/+) mice (α1(I)G349C), compared to wild type (WT) littermates. This disease system has a well-defined change in the col1α1 allele, leading to a well characterized alteration in collagen protein structure, which was directly related to altered Type I collagen nanoscale morphology. In Brt1/+ bone, the D-periodic gap/overlap spacing shows significantly greater variability on average and along the length of the bone compared to WT, although the average spacing was unchanged. Brt1/+ bone also had a significant difference in the population distribution of collagen fibrils. These changes may be due to the mutant collagen structure, or to the heterogeneity of collagen monomers in the Brt1/+ matrix. These observations at the nanoscale level provide insight into the structural basis for changes present in bone composition, geometry and mechanical integrity in Brt1/+ bones.

The present technology further demonstrates that there are no substantial differences in the nanoscale morphology of collagen between males and females. Since gender is known to play a critical role in regulating properties of the skeleton (composition, size/shape, mechanical integrity), gender-specific differences in the nanoscale morphology of Type I collagen in bone were investigated. Cortical bone from skeletally mature male and female mice was analyzed using an atomic force microscopy method, testing the hypothesis that differences would exist in the mean D-periodic axial gap/overlap spacing and population distributions of fibril morphologies as a function of gender. Results indicated that the average D-periodic gap/overlap spacing was not significantly different in male versus female bones, within the ability of the methods to detect a difference. Furthermore, there were no differences in distributions of D-periodic spacing values. These nanoscale observations suggest that although differences exist in the cells derived from male and female animals, gender-specific differences in bone size, shape and mechanical integrity are likely derived at higher organizational levels of the bone tissue hierarchy.

The following experiments and technical details illustrate aspects of methods, systems, apparatus, and compositions relating to the determination of whether a subject has a bone disease, whether the subject is at risk for developing a bone disease, and to screening a subject to determine whether they have a bone disease. In particular, the present technology can determine the distribution of Type I collagen morphologies in bone and the relation to estrogen depletion. As an experimental model, bone samples from sham-operated and estrogen-depleted animals were analyzed using the present AFM methods in order to analyze the collagen fibril morphology of normal bone. These methods could distinguish between healthy bone and bone from animals with a known disease state. As a result, the present methods increase the understanding of bone disease mechanisms and provide a complementary in vitro diagnostic technique for earlier disease detection.

The following materials and methods were employed. Regarding animals, mice from the C3H/He background strain were used with prior approval (University of Michigan, UCUCA protocol #8518). Five male mice were sacrificed at 11 weeks of age by $CO_2$ inhalation. The right femur from each mouse was harvested and the proximal (above the third trochanter) and distal ends were removed using a low-speed sectioning saw (South Bay Technology, Model 650; San Clemente, Calif.) with a diamond wafering blade (Mager Scientific) leaving approximately 7 mm of compact bone of the diaphysis. The marrow cavity of each bone was cleaned using a small tube brush.

Five-year-old Columbia-Ramboulliet cross sheep were anesthetized and ovariectomized (OVX, n=3) or subjected to a sham surgery (n=3) [Colorado State University, ACUC #03-010A-02]. After 2 years, the ewes were sacrificed with an intravenous overdose of a barbiturate, and 2 beams approximately 1.75 mm×1.75 mm×9 mm were removed from the mid-diaphysis of the left radius (Les C M, Spence C A, Vance J L, et al. Determinants of ovine compact bone viscoelastic properties: Effects of architecture, mineralization, and remodeling. Bone 2004; 35:729-38).

Atomic Force Microscopy (AFM) imaging and analysis included the following aspects. Bones were mounted to a steel disk using a thin layer of cyanoacrylate glue (mouse bones were posterior-side down), A flat polished surface was created using a 3 μm polycrystalline water-based diamond suspension and a 0.05 μm deagglomerated alumina suspension (Buehler LTD; Lake Bluff, Ill.). The bones were sonicated for 15 s to remove polishing residue and debris. To remove extrafibrillar surface mineral and expose underlying collagen fibrils, each bone was demineralized using 0.5 M EDTA at a pH of 8.0 for up to 45 min (mouse bones only required 5 min of treatment), then vigorously rinsed with ultrapure water and soaked at 4° C. for at least 16 h. EDTA is often used in bone research to remove mineral while keeping collagen and cells intact and viable, as described by Jonsson R, Tarkowski A, Klareskog L. A. Demineralization procedure for immunohistopathological use. EDTA treatment preserves lymphoid cell surface antigens. J Immunol Methods 1986: 88:109-14 and Klein-Nulend J, Burger E H, Semeins C M, Raisz L G, Pilbeam C C. Pulsating fluid flow stimulates prostaglandin release and inducible prostaglandin G/H synthase mRNA expression in primary mouse bone cells. J Bone Miner Res 1997; 12:45-51. This slow and "gentle" demineralization technique was used in the current study and allowed us to maintain the integrity of the native collagen structure along with the in fibrillar mineral; see Balooch M, Habelitz S, Kinney J H, Marshall S J, Marshall G W. Mechanical properties of mineralized collagen fibrils as influenced by demineralization. J Struct Biol 2008; 162:404-10. Before imaging, the sample was briefly sonicated to remove any surface bound mineral.

Samples were imaged in air using a PicoPlus 5500 AFM (Agilent, formerly Molecular Imaging). Images were acquired in tapping mode using a silicon cantilever with tip radius<10 nm (VistaProbes T300R, force constant 40 N/m, resonance frequency 300 kHz, length 125 μm: nanoScience Instruments; Phoenix, Ariz.) at line scan rates of 2 Hz or lower at 512 lines per frame.

Making absolute x-y distance measurements with AFM has multiple limitations. Prior to sampling, calibration of the system was performed according manufacturer guidelines. A calibration grating with a 10-μm period was imaged with the scan size set just under the range of the piezo (80 μm scan size) at 512 pixels by 512 pixels. This results in a pixel size of roughly 160 nm. To overcome limitations imposed by pixel size, multiple consecutive periods were measured. The measured period was defined as the total measured length divided by the number of periods. The calibration was adjusted until the measured period was within 50 nm of the actual 10 μm period. This calibration method results in a maximum error of 0.50%, which is less than the 1% tolerance specified by the manufacturer. For the imaging of collagen fibrils, scan sizes were reduced to 3.5 μm at 512×512 pixels. Because of the effective linearity of the piezo, error scales with the reduction of scan size reducing the 50 nm tolerance to 2.2 nm.

Image analysis included the following aspects. Images were acquired from at least 3 axial locations in each sample. At each location, 3.5 μm×3.5 μm amplitude (error) images were analyzed without leveling to investigate the D-periodic axial gap/overlap spacing, chosen as our key metric of fibril morphology. Ten fibrils from each axial location were analyzed (SPIP v4.8.2, Image Metrology; Hørsholm, Denmark). Following image capture, a rectangular region of interest (ROI) was chosen along straight segments of individual fibrils (FIG. 1). The ROI was drawn to ensure that it started and ended at the edge of a gap zone, a method which minimizes edge effects that can degrade resolution. For each evaluated fibril, a two-dimensional Fast Fourier Transform (2D FFT) was performed and the primary peak from the 2D power spectrum was analyzed to determine the value of the D-periodic gap/overlap spacing. This process decouples the measured D-Period repeat distance from both pixel size and fibril orientation. A detailed analysis of the uncertainty associated with this type of measurement in fibrils from the current study demonstrated that using at least 9 D-period repeats sets the minimum bin size for population studies at 0.8 nm. For all histograms, the bin size was therefore set at 1 nm.

Statistical analysis included the following aspects. All statistical analyses utilized SPSS (Version 16.0. SPSS Inc.). For all investigations, a value of p<0.05 was considered significant. To investigate differences in fibril morphology between species and due to estrogen deficiency, D-periodic axial spacing values measured from an individual sample were pooled, yielding an average value for that sample. The values from mice (n=5), sham sheep (n=6) and OVX sheep (n=5) were then compared using one-way ANOVA with post hoc Bonferroni tests.

To examine differences in the distribution of fibril morphology between sham and OVX groups, the Cumulative Distribution Function (CDF) of each group was computed. The CDF shows what fraction of a given sample is contained up to a particular value, easily demonstrating differences between distributions in both mean and standard deviation. In FIG. 5b, Cumulative Group Total (%) is used on the y-axis to make it clear that the CDF is a percentage within each group up to each spacing value. To test for statistical significance between distributions, Kolmogorov-Smirnov (K-S) tests were then applied to the data. This test is sensitive to changes in both the mean value and standard deviation of a distribution.

The following results were obtained. To quantitatively assess the axial gap/overlap spacing in murine cortical bone as a baseline, femora from 11-week-old male mice of the C3H/He background strain were used. In the intracortical bone along the anterior surface of the diaphysis, 3 axial locations were analyzed. At each axial location, a 10 μm×10 μm scan was performed to find suitable sites for closer inspection. FIG. 2 shows a representative 3D rendering of a bone surface displaying bundles of well-oriented fibrils surrounded by less organized fibrils in a woven configuration. At least 10 fibrils were chosen in each axial location, yielding at least 30 measurements from each bone. In total, 193 fibrils were analyzed.

For each of the analyzed bones, the measurements within each bone were pooled to yield the mean fibril spacing for that bone. These mean values ranged from 67.7 nm to 69.0 nm (FIG. 3a), with an overall mean axial spacing for all 5 bones of 68.3±2.4 nm. The median value for all 193 measures of 68.2 nm was in good agreement with the mean. The dashed horizontal lines in FIGS. 3a and 4 are for reference and correspond to the 67 nm axial spacing that is predicted by the Hodge-Petruska model (Hodge A J, Petruska J A. Recent studies with the electron microscope on ordered aggregates of the tropocollagen molecule. In: Ramachandran G N, editor. Aspects of protein structure. New York; Academic Press; 1963. p. 289). As noted in the materials and methods, the ability to measure absolute distances with AFM was limited by the about 2.2 nm tolerance set during the calibration of our system. Therefore, it is not possible to state that there is an absolute difference between the 68.3 nm mean in the mouse fibrils and the 67 nm value predicted by Hodge and Petruska. The histogram of all 193 fibrils shows that there is a distribution of spacings ranging from 63 nm to 74 nm (FIG. 3b).

Using a model of estrogen-depletion in sheep, it was hypothesized that it would be possible to distinguish between normal bone and bone from animals with a known disease state by monitoring changes in the distribution of collagen fibril morphologies. Samples from ovariectomized (OVX) and sham-operated sheep were processed as described in the materials and methods. It was found that the fibrils from the sham sheep were similar in terms of mean (68.0±2.6 nm) and distribution when statistically compared with mouse fibrils (FIG. 4, p=1.00 for ANOVA, p=0.319 for KS test). However, comparison of sham samples (n=6) to OVX samples (n=5) showed striking differences. The mean from the OVX samples was 65.9±3.1 nm. When the mean values from Sham and OVX samples were compared by one-way ANOVA, there was a significant effect of estrogen-depletion on the fibril spacing (p=0.048), When the fibrils in each group are viewed in histogram form, there are different populations of fibrils within the 2 groups (FIG. 5). The bins which contain the main population of fibrils in each group were selected such that they contain the mean of the sham fibrils ±1 standard deviation (65 nm to 71 nm). The sham bones had a population of fibrils (11.5% of total fibril measured) with spacings of 72 nm or greater which was almost completely absent from the OVX group (1.8%). Similarly, the OVX bones had a population of fibrils with spacings of 64 nm or less (28.0%) which was less prominent in the sham bones (7.1%). When compared using a K-S test, the CDFs from the groups was significantly different (p<0.001) indicating a significant difference in the population distributions of the groups (FIG. 5b).

Our data indicate that as opposed to a single value, normal bone contains a distribution of collagen fibril D-periodic axial gap/overlap spacings. This measure captures many aspects of the fibril hierarchy and can be related to the state of the individual triple helices, posttranslational modifications and cross-linking. By monitoring this distribution in normal bone and bone from estrogen-depleted animals, we have demonstrated the ability to detect disease-induced differences in the Type I collagen ultrastructure of bone.

In this study, 2D FFTs were used to determine the value of the D-periodic gap/overlap spacing (FIG. 1). At least one other study has used analysis by FFT to derive spacing data from AFM images of collagen (Habelitz S, Balooch M, Marshall S J, Balooch G, Marshall Jr G W, In situ atomic force microscopy of partially demineralized human dentin collagen fibrils, J Struct Biol 2002; 138:227-36). This study relied on the 1D FFT, a method which allows the user to determine the power spectrum of the wavelength component along a single line in an image. This method is dependent on the angular orientation of a line that is drawn on the collagen fibril by the user and can lead to errors in the measured spacing values. From our calculation, as little as a 5° deviation in the line that is drawn from the normal direction of the fibril spacing can alter the measured spacing by as much as 5% to 10%, depending on the measured length of the fibril. A 10% error on a measurement of a 67-nm fibril means that the spacing value could range from 60-74 nm, making it impossible to detect the type of changes in fibril morphology seen and discussed herein. The combination of more accurate measures and the assessment of variability associated with those measures provide us with confidence that the values we obtain are true characteristics of the tissues being measured.

To quantitatively assess the Type I collagen morphology in murine compact bone as a baseline, femora from 11-week-old male mice from the C3H/He background strain were used. The use of a specific age, gender, and background strain of mouse guarantees that the known influence of these properties on skeletal structure and function were avoided. Further, by investigating multiple axial locations along the length of one type of bone, the effect of variations within and between bones was reduced. FIG. 2 shows a representative 3D rendering of a bone surface displaying bundles of well-oriented fibrils surrounded by less organized fibrils in a woven configuration.

Using 2D FFT analyses, we found a distribution of spacings in normal murine bone ranging from 63 nm to 74 nm (FIG. 3). Although the most commonly accepted value for this D-periodic spacing is 67 nm (as predicted by Hodge and Petruska), this value is based on a theoretical model of a single collagen fibril in isolation. As mentioned above, the ability to accurately measure absolute distances using AFM is intrinsically limited by the calibration process. The error associated with these absolute measurements therefore reduces our ability to make a comparison of the absolute mean to the expected 67 nm value, as the difference between these values is within the error of the technique. However, the strength of this study is that a distribution of spacing values was present in normal tissue. This range of values is a real observation and is not impacted by the absolute error. The concept of a distribution is often overlooked in measurements of collagen, and the mean value is reported without explanation.

A study in dentin, for example, showed a distribution in fibril spacings, but reported that there was a "relatively narrow distribution" in the measurements around 67 nm (Habelitz S, Balooch M, Marshall S J, Balooch G, Marshall Jr G W. In situ atomic force microscopy of partially demineralized human dentin collagen fibrils. J Struct Biol 2002; 138:227-36). We hypothesize that although the mean value of the D-periodic spacing in a mineralized fibril is important, the distribution itself may have even greater significance. This distribution of fibril morphologies is found in wild type bone meaning that it is a fundamental property of normal tissue. The influences that a distribution of collagen morphologies (versus a single value) could have on the mechanical properties of the tissue are profound. Bone is a heterogeneous tissue with anisotropic mechanical properties. Given that a whole bone is typically under a complex loading state including tension, compression and shear, it is imperative that the structure as a whole be mechanically competent in multiple directions. The material itself is much more specialized and the anisotropic tissue properties that contribute to overall mechanical competence begin at the most fundamental levels of the tissue hierarchy. It is likely that the distribution of fibril morphologies measured here is partially responsible.

Alterations in the distribution of fibril morphology in cases of disease may indicate flaws in the collagen fibrils from misalignment or over-modification of the individual collagen molecules within the fibrils, changes that could be compensated for over larger length scales. Using a model of estrogen-depletion in sheep, it was hypothesized that it would be possible to distinguish between normal bone and bone from animals with a known disease state by monitoring changes in this distribution. The fibrils from the sham sheep were similar in terms of mean and distribution compared with the normal mouse fibrils (FIG. 4), verifying the utility of this method in different species. However, a comparison of sham sheep to OVX sheep showed striking differences both in terms of overall mean as well as in distribution (FIGS. 4 and 5). This ability to measure fibril morphology and to distinguish between normal and diseased bone not only provides a powerful method to study the mechanism of disease at the nanoscale, but it also has important implications to the diagnosis of disease in bone and other collagenous tissues (e.g., dentin, tendon, skin, ligament).

The current gold-standard for diagnosis of osteoporosis focuses exclusively on BMD, as measured from a 2D DEXA projection, and is therefore dependent on bone size and shape. Further, using BMD to diagnose osteoporosis is problematic, as normal BMD does not guarantee protection from fracture and many osteoporosis cases do not become clinically evident until fracture occurs. The current study shows that measuring properties of the organic matrix may provide powerful complementary information to BMD, as changes in collagen may become apparent earlier in the progression of the disease. Although this method would currently require a biopsy, something that is a standard practice for the diagnosis of many bone diseases, the benefit of earlier diagnosis and treatment may outweigh the risk.

Although AFM requires less sample preparation than other high resolution imaging modalities, there is still the possibility of artifacts for sample preparation and imaging. Samples in the current study were imaged in air meaning that contraction of fibrils could occur from dehydration. However, most examples of contraction were observed using electron microscopy which fully dehydrates the tissue and requires ultra-high vacuum in our experience imaging bone, dentin, and tendon from multiple species and from normal and diseased animals, contraction of fibril spacing or the appearance of new fibril populations due to dehydration has never been observed.

The collagen in bone is impregnated with and surrounded by mineral which must be removed. After 30 min of continuous treatment with 10% citric acid, intrafibrillar mineral is protected from demineralization. Further, treatment with EDTA removes extrafibrilla mineral while leaving the underlying collagen intact (Kindt J H, Thurner P J, Lauer M E, et al. In situ observation of fluoride-ion-induced hydroxyapatite-collagen detachment on bone fracture surfaces by atomic force microscopy. Nanotechnology 2007; 135102:18). EDTA can remove mineral while keeping cells and collagen intact and viable. Mouse bones were only treated for about 5 min with EDTA while the sheep bones required up to 45 min. There were no differences in either mean spacing value or in the distribution of fibril morphologies between the mouse bones and the sham sheep bones. Further the comparison between bone, dentin (also mineralized) and tail tendon (not mineralized and, therefore, not treated with EDTA) showed no differences in mean fibril spacing. This comparison between samples which required sonication (bones and teeth) and samples which did not (tendons) further indicates that the effects of sonication were minimal, All samples in the current study were imaged under identical conditions and we are interested only in relative differences between groups. Therefore the differences seen here are likely true disease-induced changes in Type I collagen morphology.

In sum, the current technology demonstrates the ability to utilize AFM imaging to make quantitative assessments of the distribution of collagen fibril morphologies in bone. It is clearly shown that normal bone contains a distribution of collagen fibril morphologies and that changes in this distribution can be directly related to disease state. Osteoporosis is a significant medical and economic burden facing our society and is projected to worsen with the aging population. Although more research on the causes of this disease is important, early diagnosis and treatment is imperative. Monitoring changes in the fibril morphology distribution as a function of disease not only increases our fundamental understanding of bone as a material, but also provides important insight into disease progression and offers the possibility of a much-needed in vitro procedure to complement the use of BMD for disease diagnosis.

The present technology further demonstrates that Type I collagen exists as a distribution of nanoscale morphologies in teeth, bones, and tendons. Collagens are the most abundant structural proteins in animals. In humans, there are currently 28 proteins known as collagens serving a variety of structural roles including shaping and organizing extracellular matrices (ECM), providing a scaffolding for tissue formation, cell adhesion and migration, as well serving as the principal source of tensile strength in animal tissues. The hallmark characteristic of collagen is a macromolecule composed of trimeric polypeptide chains, each comprising regions including a repeating Gly-X-Y triplet (X and Y are often proline and hydroxyproline, respectively). One major classification of collagen is the fibrillar-forming type, which has an approximately 300 nm long, uninterrupted triple helix (with the exceptions of Type XXIV and XXVII).

Type I collagen is archetypal in that it is trimeric, possesses an uninterrupted Gly-X-Y triple helix, and assembles into structural fibrils. With the exception of cartilaginous tissues, Type I collagen is found throughout the body in tissues such as teeth, bones, tendons, skin, arterial walls, and the cornea. Type I collagen is also synthesized in response to injury and is present in scar tissue. On the basis of the seminal work of Hodge and Petruska in 1963 (and earlier work by many others), the primary morphological characteristic of Type I collagen fibrils, the D-periodic axial gap/overlap spacing, was shown to be 67 nm based on theoretical models of a single collagen fibril in isolation. In the 47 years since this assertion, X-ray diffraction and electron microscopy studies have supported this singular spacing value within the error of the individual technique. Given the complexity of the collagen fibril itself, the range of tissues in which these fibrils are incorporated, and the potential for morphology variation with disease, it seems unlikely that a single spacing value would exist for all fibrils. A recent study using atomic force microscopy (AFM) noted a distribution of fibril spacing values in dentin, but did not statistically analyze the distribution or discuss its biological or mechanical significance (Habelitz, S.; Balooch, M.; Marshall, S. J.; Balooch, G.; Marshall, G. W., Jr. J. Struct. Biol. 2002, 138, 227-236).

Measuring and understanding morphological features of the ultrastructure of collagen in collagen-based tissues is imperative to our understanding of normal tissue architecture. The need for accurate quantitative analytical methods to assess collagen's nanoscale morphology with as little disruption to the tissue as possible has prompted us to study the collagen ultrastructure of various tissues using AFM. As opposed to other methods which are used to image the Type I collagen ultrastructure of tissues, samples imaged using AFM remain intact to a greater degree, increasing confidence that measured properties are sample characteristics rather than artifacts of processing or imaging. Although AFM has been used to image the collagen matrix in mineralized dentin and bone, and other nonmineralized tissues, the current study uses a quantitative and statistically powered technique to analyze the nanoscale morphology of individual Type I collagen fibrils in multiple tissues from the same animal.

In the current study, it was hypothesized that AFM could be used to image and quantitatively analyze the morphology of Type I collagen fibrils in fully intact and mineralized teeth and bones, as well as in nonmineralized tendons, to learn more about the normal nanoscale properties of these materials. These three tissues were chosen based on their differences in cellular origin and function. Further, since tendons lack mineral under normal physiological conditions, tendon samples served as an internal control to verify that the demineralization process used on bone and dentin samples did not disrupt the native collagen structure of these tissues within the detection limits of the AFM methodology.

The following materials and methods were employed. With respect to animals, eight-week-old male mice from the mixed Sv129/CD-1/C57BL/6S background strain were used with prior approval (University of Michigan, UCUCA protocol #09637). After sacrifice by $CO_2$ inhalation, femora, mandibular incisors, and tails were harvested, wrapped in gauze soaked with calcium-buffered saline, and stored at −20° C.

Atomic Force Microscopy (AFM) imaging and analysis included the following aspects. Before use, the proximal (above the third trochanter) and distal ends of each left femur were removed using a low-speed sectioning saw (South Bay Technology, model 650; San Clemente, Calif.) with a diamond wafering blade (Mager Scientific) leaving approximately 7 mm of compact bone of the diaphysis (FIG. 1). The marrow cavity of each bone was cleaned using a small tube brush.

Mandibular incisors were cleaned of soft tissue and surrounding bone. Bones (anterior side facing up) and teeth (lateral side facing up) were mounted onto a steel disk using a thin layer of cyanoacrylate glue. A flat polished surface was created using a 3 µm polycrystalline water-based diamond suspension and a 0.05 µm deagglomerated alumina suspension (Buehler LTD; Lake Bluff, Ill.). This polishing exposed intracortical bone in the bone samples and dentin in the teeth samples. The bones and teeth were sonicated for 15 s to remove polishing residue and debris. To remove extrafibrillar surface mineral and expose underlying collagen fibrils, each bone and tooth was demineralized using 0.5 M EDTA at a pH of 8.0 for up to 15 min, then vigorously rinsed with ultrapure water and soaked at 4° C. for at least 16 h. EDTA is often used in mineralized tissue research to remove mineral while keeping collagen and cells intact and viable. This demineralization technique is slower than other treatments and allowed us to maintain the integrity of the native collagen structure along with the intrafibrillar mineral. Before imaging, each sample was briefly sonicated to remove any mineral that was still bound to the surface.

To isolate tendons from each tail, the tip of the tail was removed using a scalpel. The skin was peeled back at the base of the tail and removed in a base-to-tip direction, exposing the underlying tendons. Tendons were removed whole, minced using a scalpel and scissors, and then homogenized in 1-2 mL of ultrapure water to disrupt the fascicle structure and release collagen fibrils. Fibril containing solutions were deposited onto freshly cleaved mica surfaces and allowed to dry at room temperature.

Samples were imaged in air using a PicoPlus 5500 AFM (Agilent). Dentin and bone were imaged in tapping mode using silicon cantilevers (VistaProbes T300R, tip radius<10 nm, force constant 40 N/m, resonance frequency 300 kHz; nanoScience Instruments; Phoenix, Ariz.). Tendon fibrils were imaged in contact mode using silicon nitride cantilevers (Veeco DNP, tip radius about 20 nm, force constant 0.58 N/m). Images were acquired from 3 locations in each of 5 teeth, 9 locations in each of 4 bones (designated 1-9 beginning at the proximal end of the sample, FIG. 6), and several locations in each of 4 tendon samples. At each location, 3.5 µm×3.5 µm amplitude or deflection images were analyzed to investigate the D-periodic spacing. In teeth, 15-20 fibrils were analyzed in each location. In bones, 5-10 fibrils were analyzed in each location (with the exception of 1 bone which lost locations 8 and 9 during polishing). In each tendon sample, 35-50 fibrils were analyzed. Representative images and line scans from each tissue type are shown in FIG. 7.

Image Analysis included the following aspects. After image capture, a rectangular region of interest (ROI) was chosen along straight segments of individual fibrils (FIG. 3a; SPIP v 4.8.2, Image Metrology; Hørsholm, Denmark, FIG. 7). The ROI was drawn to ensure that it started and ended at the edge of a gap zone, which minimizes edge effects that can degrade resolution. For each evaluated fibril, a two-dimensional fast Fourier transform 2D FFT) was performed and the primary peak from the 2D power spectrum was used to determine the value of the D-periodic gap/overlap spacing (FIG. 8b). This process decouples the measured D-Period repeat distance from both pixel size and fibril orientation. In total, 291 dentin fibrils, 288 bone fibrils, and 160 tendon fibrils were analyzed.

Making absolute x-y distance measurements with AFM can have limitations. Prior to sampling, calibration of the system was performed according manufacturer guidelines. A calibration grating with a 10 µm period was imaged with the scan size set just under the range of the piezo (80 µm scan size) at 512 pixels by 512 pixels. This results in a pixel size of roughly 160 nm. To overcome limitations imposed by pixel size, multiple consecutive periods were measured. The measured period was defined as the total measured length divided by the number of periods. The calibration was adjusted until the measured period was within 25 nm of the actual 10 µm period. This calibration method results in a maximum error of 0.25%, which is less than the 1% tolerance specified by the manufacturer. For the imaging of collagen fibrils, scan sizes were reduced to 3.5 µm at 512×512 pixels. Because of the effective linearity of the piezo, error scales with the reduction of scan size reducing the 25 nm tolerance to 1.1 nm.

Statistical Analysis included the following aspects. All statistical analyses utilized SPSS (version 16.0, SPSS Inc.). For all investigations, a value of $p<0.05$ was considered significant. To investigate differences in fibril morphology as a function of tissue type, D-periodic axial spacing values measured from an individual sample were pooled, yielding an average value for that sample. The values from dentin (n=5), bone (n=4), and tendon (n=4) were then compared by one way ANOVA with posthoc Bonferroni tests.

To examine differences in the distribution of fibril morphology among tissue types, histograms and the cumulative distribution function (CDF) of each group were computed. The CDF shows what fraction of a given sample is contained up to a particular value, easily demonstrating differences among distributions in both mean and standard deviation. In FIG. 11b, cumulative total (%) is used on the y-axis to make it clear that the CDF is a percentage within each group up to each spacing value. To test for statistical significance between distributions, Kolmogorov-Smirnov (K-S) tests were then applied to the data. This test is sensitive to changes in both the mean value and standard deviation of a distribution.

The D-periodic axial gap/overlap spacing was chosen as the key metric of fibril morphology. This measure captures aspects of fibril structure which may be related to the state of the individual molecular triple helices, post-translational modifications, and cross-linking. The most commonly accepted value for the D-periodic spacing of Type I collagen is 67 nm (as predicted by Hodge and Petruska), but this value is based on a theoretical model of a single collagen fibril in isolation. The molecular origin of this morphological feature has not been completely elucidated. A recent study performed AFM and TEM analyses on identical collagen fibrils (Lin, A. C.; Goh, M. C. Proteins Struct., Funct., Genet. 2002, 49, 378-384). The paper suggested that the taller protrusions seen on the surface of collagen fibrils using AFM register perfectly with the dark bands seen in TEM, suggesting that there is more material in these bumps and that this material is better at scattering electrons. As mentioned by the authors, this observation does not rule out the existence of gap zones as proposed by Hodge and Petruska. Regardless of the origin of the D-periodic spacing, this morphological feature is well-resolved with AFM and easy to quantify.

To quantitatively assess the D-periodic spacing in Type I collagen-based tissues as a function of tissue type, mandibular incisors, femora, and tails were harvested from 8-week-old male mice. The use of a specific age, gender, and background strain of mouse guarantees that the known influence of these properties on skeletal structure and function was avoided.

Along the length of each bone, measurements were made at nine axial locations (FIG. 6). By pooling data from the four bones at each of the nine locations and analyzing the D-periodic spacing, it was confirmed that there were no systemic changes in Type I collagen morphology as a function of axial location in the bone (FIG. 9). The boxes represent the middle 50% of the data, and the whiskers depict the data extremes. The diamond is the mean, and the line within the box is the median of each group. The dashed horizontal line is for reference and corresponds to the 67 nm axial spacing that is predicted by the Hodge-Petruska model. This type of data presentation is only possible for the bone samples. Dentin samples were measured from three locations in each tooth. However, because of differences in tooth geometry, these locations were not identical from tooth to tooth. Further, the tendon samples were adsorbed on mica so anatomical location is not applicable.

Measurements within each tooth, bone, and tail sample were pooled to yield the mean fibril spacing for that sample. Tooth (n=5), bone (n=4), and tendon samples (n=4) were then compared; the overall mean values within each tissue type were 67.8, 67.3, and 67.9 nm for dentin, bone, and tendon, respectively (FIG. 10). On the basis of system calibration, the ability to measure absolute distances has an error of approximately 1.1 nm. Therefore, it is not possible to state that the measured means in this study are different from the 67 nm value predicted by Hodge and Petruska. When the mean values in each group were compared by one way ANOVA with posthoc Bonferroni tests, no differences were present between any of the groups (FIG. 10B; a p-value of <0.05 was considered significant).

FIG. 11 shows that a distribution of fibril morphologies existed in each group. The concept of a distribution is often overlooked in measurements of collagen, and the mean value for the D-periodic spacing is sometimes reported without explanation. The main population of fibrils in each group was selected such that the bins contained the mean of the bone fibrils (±1 standard deviation (66 to 69 nm, FIG. 11a). Within this range, 75% of bone fibrils were found in comparison to 85% for dentin and 60% for tendon fibrils. As a second method to visualize the distributions, the cumulative distribution function (CDF) was computed from the measurements in each group (FIG. 11b). To test for statistical significance between distributions, Kolmogorov-Smirnov (K-S) tests were applied to the data. This test is sensitive to changes in both the mean value and standard deviation of a distribution. The distributions from the three tissue types were statistically distinguishable from one another (FIG. 11b: dentin vs. bone, p<0.001; dentin vs. tendon, p=0.004; bone vs. tendon; p<0.001). Despite these differences, the presence of a distribution was a common feature in all three tissues, indicating that a distribution of fibril morphologies is a defining nanoscale characteristic of Type I collagen.

The presence of a distribution in fibrils is interesting and important, as this distribution may hold the key to understanding important aspects of the ultrastructure of many collagen-based tissues. Explaining the reasons behind the presence of a distribution in fibril morphologies is not trivial. Because of the structural hierarchy of collagen fibrils, a distribution in the D-periodic spacing near the ideal value predicted by Hodge and Petruska is most likely driven by alterations in the end-to-end spacing of collagen molecules within the fibril, or by a change in the tightness of the twist of the fibril. Either of these mechanisms could cause the measured D-period spacing at the fibrillar-level to change. Another possibility is the presence of proteins both within and on the surface of collagen fibrils, which may lead to changes in the observed spacings. Another potential source of variation is the presence of intramolecular and intermolecular crosslinks, which could not only add heterogeneity to the structure, but also allow the spacing to further change as the crosslinks mature.

One drawback when working with mineralized tissues like bone and dentin is that, in order to analyze the organic component by AFM, some portion of the inorganic mineral must be removed to expose the underlying structure. Regardless of the method used, there is the possibility that this treatment could have important effects on the properties that one hopes to measure. Many methods are used in the literature to remove this mineral for imaging studies such as AFM. A majority of studies use some form of acid which etches mineral from the surface to expose collagen. In our hands, these methods worked rapidly and often completely destroyed the surface (e.g., craterlike hole would appear on the surface within 1-2 min, but no defined collagen fibrils were visible). In contrast to these acid treatments, EDTA is a chelating agent which is slow at removing calcium from bone and is close to physiological pH. With long-term treatment (days to weeks), EDTA can fully demineralize bone and dentin. In fact, EDTA is often used to remove mineral and liberate trapped osteocytes for cell culture experiments. In the current study, every effort was made to treat the samples for as little time as possible to expose the underlying collagen fibrils.

It is important to keep in mind that, although reports vary, roughly ⅓ of the mineral present in the extracellular matrix (ECM) of mineralized tissues is intrafibrillar (i.e., present within the collagen fibrils themselves). This fact suggests that short periods of EDTA treatment are likely to preferentially remove extrafibrillar mineral first, leaving behind the intrafibrillar mineral which helps to stabilize the structure of the ECM. Two recent AFM studies directly assess the effects of citric acid (Balooch, M.; Habelitz, S.; Kinney, J. H.; Marshall, S. J.; Marshall, G. W. J. Struct. Biol. 2008, 162, 404-410.) or EDTA (Kindt, J. H.; Thurner, P. J.; Lauer, M. E.; Bosma, B. L.; Schitter, G.; Fantner, G. E.; Izumi, M.; Weaver, J. C.; Morse, D. E.; Hansma, P. K. Nanotechnology 2007, 18, 135102) on mineralized collagen fibrils. The first paper follows the effects of citric acid over time and found that intrafibrillar mineral is protected from demineralization, even after 30 min of continuous treatment. The second study showed that treatment with both NaF and EDTA removed extrafibrillar mineral while leaving the underlying collagen structure intact. In the current study, nonmineralized tendon samples served as an internal control to verify that the demineralization process used on bone and dentin samples did not alter collagen structure within the ability of our AFM technique to detect changes in morphology. The comparison of tendon to bone and dentin also verified that the presence of mineral is not the source of the observed distributions in bone and dentin.

The tissues analyzed in the current study serve a variety of mechanical roles. Dentin is less mineralized and less brittle than the enamel that covers it and primarily supports compressive loads from mastication (dentin in the mouse mandibular incisor may also be subject to tensile loads given its shape). Tendons provide a link between bones and muscles and are subject to tensile loading. Bone is a heterogeneous tissue, and depending on location, bone can be subjected to a highly complex loading state including tension, compression, and torsion. Despite these differences in mechanical need, all three tissues displayed a similar distribution of collagen fibril morphologies. The influences that such a distribution may have on the mechanical integrity of a tissue are unknown. However, it is possible that, as the spacing in a fibril gets shorter, less space is available in the fibril for the presence of water or mature crosslinks. This could detrimentally impact the viscoelastic and post-yield properties of the tissue, while possibly leading to a stiffer fibril. The impacts that such changes have on the structural-level properties of a tissue are complicated given the hierarchical complexity of collagen-containing tissues.

Given the ubiquitous nature of Type I collagen in animals, and the number of disease that can affect collagen-containing tissues, it seems probable that alterations in the Type I collagen ultrastructure will occur with disease. In fact, the present technology shows that for samples from normal and estrogen-depleted sheep (all of which were treated and imaged in exactly the same way), not only is the mean fibril spacing significantly changed, but so too is the distribution of fibril morphologies. The fact that disease-induced changes in the distribution of fibril morphologies were observed further indicates that the presence of a distribution is not driven by artifact. Age-dependent diseases such as estrogen-depletion-related osteoporosis, which is not correlated with genetic alteration, can lead to collagen pathologies which are detectable using AFM. Therefore, monitoring this distribution represents a new diagnostic technique for disease in a number of collagen-based tissues.

Some concern may be raised over the imaging conditions used in the current study. Dehydration of collagen fibrils has been observed to change the normal d-periodic spacing of the fibrils. The majority of these observations were made using electron microscopy, a method that not only fully dehydrates the tissue, but also requires ultrahigh vacuum. When using AFM in the current technology (a method that does not require ultrahigh vacuum), tissues were processed and stored wet. Just before imaging, the surface of the bones and teeth were briefly blown dry with nitrogen and imaged immediately under atmospheric pressure. The tendon samples are allowed to dry in air for around 1 h, and then imaged under the same conditions. It is likely that the sample was not fully dehydrated even after the entire sample had been imaged. Regardless, all samples in the current technology were imaged under identical conditions, and only relative differences between tissue types were analyzed.

In sum, the present technology demonstrates that, regardless of cellular origin or anatomical location, normal Type I collagen-based tissues contain a distribution of nanoscale collagen morphologies as measured using the D-periodic gap/overlap spacing. The mean differences in the D-period spacing are not statistically significant; however, the differences in the distributions of the D-period spacing as a function of tissue type are statistically significant. This is a new and important observation on the nanoscale ultrastructure of the most abundant protein in animals. The presence of this distribution may hold powerful information about the ultrastructure of collagen-based tissues. Further, monitoring this distribution represents a new diagnostic technique for disease in a number of collagen based-tissues.

The present technology further demonstrates that the nanoscale morphology of type I collagen is altered in the Brt1 mouse model of Osteogenesis Imperfecta (OI). Type I collagen forms the scaffolding upon which all bones are built. Mutations in the genes encoding the α chains which form the triple helical collagen molecule can cause diseases of bone and other tissues such as OI, or brittle bone disease, and some forms of Ehlers-Danlos Syndrome. Type I collagen is a heterotrimeric molecule composed of two α1 chains and one α2 chain. Human OI results primarily from point mutations that cause the substitution of a triple helical glycine residue (80%) or splice site mutations (20%) in the genes encoding the α1 or α2 chains of Type I collagen. The disease displays a wide spectrum of clinical severities, with more severe forms arising from changes in the primary amino acid sequence. These changes in alpha chain structure result in delayed protein folding and over-modification of the collagen triple helix, and decrease collagen quality, although disease severity does not correlate with the extent of collagen over-modification. Milder forms of dominant OI arise from null mutations in one Type I collagen allele, resulting in an underproduction of normal collagen. Depending on the severity of the disease, symptoms range from susceptibility to fracture from mild trauma to perinatal lethality.

Correlations between genotype and phenotype in OI utilizing over 800 mutations revealed that mutations in the Major Ligand Binding Regions in the α1 chain and the proteoglycan binding regions in the α2 chain were almost entirely lethal. Histomorphometry of OI bone has shown that surface-based remodeling parameters are increased in all forms of OI but that mineralization defects are not present (with the possible exception of Type VI OI). However, correlations between genotype and collagen structure in OI bone have not been made. The Brittle (Brt1) mouse, a model of human Type IV OI which has a classical glycine substitution (G349C) in one col1α1 allele, was created to study how specific changes in the amino acid sequence of collagen can lead to OI phenotypic characteristics.

The need for quantitative analytical methods to assess the nanoscale morphology of collagen in bone without tissue disruption has prompted us to study the collagen ultrastructure of bone using atomic force microscopy (AFM). In comparison to other high-resolution methods used to assess the nanoscale properties of bone and other mineralized tissues, AFM is less destructive and requires less sample preparation, implying that measured properties are less likely artifacts of sample processing or imaging. It was previously shown that normal Type I collagen-based tissues, including bone, contain a distribution of Type I collagen fibril morphologies. We further demonstrated that estrogen-depletion in sheep leads to a significant change in this distribution in bone. However, because the effects of estrogen on collagen structure are not well understood, it was not possible to ascribe a mechanism to these changes in collagen morphology. In the experiments presented below, AFM was used to image and quantitatively analyze the morphology of Type I collagen fibrils in intact and mineralized bones from wild type (WT) and heterozygous (Brt1/+) mice. This disease system has a well-defined change in the col1α1 allele and in collagen protein structure, which are directly related to altered Type I collagen nanoscale morphology. It was hypothesized that changes in the mean D-periodic axial gap/overlap spacing as well as alterations in the population distribution of fibril morphologies, might be present in diseased fibrils from Brt1/+ mice in comparison to their WT littermates. Although the average D-periodic gap/overlap spacing was not significantly different in Brt1/+ versus WT bone, the D-periodic gap/overlap spacing in Brt1/+ bone had greater variability overall and along the length of the bone. A significant difference in the collagen population distributions was also present in Brt1/+ bone. These nanoscale observations provide insight into the structural basis for changes present in bone composition, geometry and mechanical integrity in Brt1/+ bones.

Materials and methods employed include the following aspects. Brt1/+ and WT mice from the mixed Sv129/CD-1/C57BL/6S background strain were used with prior approval of the NICHD Animal Care Committee (protocol # ASP 09-023) and were sacrificed by lethal injection. Femurs from two month-old male wild type (WT, n=4) and Brt1/+ (n=4) mice were harvested and stripped of soft tissue before processing for imaging Atomic Force Microscopy (AFM) imaging and analysis included the following aspects. Before use, the proximal (above the third trochanter) and distal ends of each right femur were removed using a low-speed sectioning saw (FIG. 6). The marrow cavity of each bone was cleaned using a small tube brush. Bones were mounted, anterior-side up, to a steel disk using a thin layer of cyanoacrylate glue. A flat polished surface of intracortical bone was created using a 3 μm polycrystalline water-based diamond suspension and a 0.05 μm deagglomerated alumina suspension (Buehler LTD; Lake Bluff, Ill.). The bones were sonicated for 15 seconds to remove polishing residue and debris. To remove extrafibrillar surface mineral and expose underlying collagen fibrils, the surface of each bone was demineralized using 0.5M EDTA at a pH of 8.0 for 15 minutes, then vigorously rinsed with ultrapure water and soaked at 4° C. for at least 16 hours. EDTA is often used in mineralized tissue research to remove mineral while keeping collagen and cells intact and viable. Before imaging, each sample was briefly sonicated to remove any mineral that was still bound to the surface.

Samples were imaged in air using a PicoPlus 5500 AFM (Agilent). Images were acquired in tapping mode using silicon cantilevers (VistaProbes T300R, tip radius<10 nm, force constant 40 N/m, resonance frequency 300 kHz; nanoScience Instruments; Phoenix, Ariz.) at line scan rates of 2 Hz or lower at 512 lines per frame.

Making absolute x-y distance measurements with AFM can present limitations. Prior to sampling, calibration of the system was performed according manufacturer guidelines. A calibration grating with a 10 μm period was imaged with the scan size set just under the range of the piezo (80 μm scan size) at 512 pixels by 512 pixels. This results in a pixel size of roughly 160 nm. To overcome limitations imposed by pixel size, multiple consecutive periods were measured. The measured period was defined as the total measured length divided by the number of periods. The calibration was adjusted until the measured period was within 25 nm of the actual 10 μm period. This calibration method results in a maximum error of 0.25%, which is less than the 1% tolerance specified by the manufacturer. For the imaging of collagen fibrils, scan sizes were reduced to 3.5 μm at 512×512 pixels. Because of the effective linearity of the piezo, error scales with the reduction of scan size, reducing the 25 nm tolerance to 1.1 nm.

Images were acquired from 9 axial locations in each bone sample (designated 1-9 beginning at the proximal end of the sample, FIG. 6). At each location, 3.5 μm×3.5 μm amplitude images were analyzed to investigate the D-periodic axial gap/overlap spacing, chosen as our key metric of fibril morphology (FIG. 12). Five to ten fibrils from each axial location were analyzed (SPIP v5.0.6, Image Metrology; Hørsholm, Denmark). Following image capture, a rectangular region of interest (ROI) was chosen along straight segments of individual fibrils (FIG. 13). The ROI was drawn to ensure that it started and ended at the edge of a gap zone, a method which minimizes edge effects that can degrade resolution. For each evaluated fibril, a two dimensional Fast Fourier Transform (2D FFT) was performed and the primary peak from the 2D power spectrum was analyzed to determine the value of the D-periodic gap/overlap spacing. This process decouples the measured D-Period repeat distance from both pixel size and fibril orientation. A detailed analysis of the uncertainty associated with this type of measurement sets the minimum bin size for population studies at 0.8 nm. For all histograms, the bin size was therefore set at 1 nm.

All statistical analyses utilized SPSS (Version 16.0, SPSS Inc.). For all investigations, a value of $p<0.05$ was considered significant. To investigate differences in fibril morphology as a function of genotype, D-periodic axial spacing values measured from an individual sample were pooled, yielding an average value for that sample. The values from WT (n=4) and Brt1/+ (n=4) mice were then compared using One Way ANOVA.

To examine differences in the distribution of fibril morphology between genotypes, histograms and the Cumulative Distribution Function (CDF) of each group were computed. The CDF shows the fraction of a given sample which is contained up to a particular value, easily demonstrating differences between distributions in both mean and standard deviation. To test for statistically significant differences between distributions, Kolmogorov-Smirnov (K-S) tests were applied to the data. This test is sensitive to changes in both the mean value and standard deviation of a distribution.

The D-periodic axial gap/overlap spacing was chosen as the key metric of fibril morphology (FIG. 12). This measure captures aspects of fibril structure which may be related to the state of the individual molecular triple helices, post-translational modifications and cross-linking. To quantitatively assess the axial gap/overlap spacing in murine cortical bone as a function of OI genotype, femora from 2 month old male mice were used. In the intracortical bone along the anterior surface of the diaphysis, 9 locations were analyzed in each sample. Five to ten fibrils were analyzed at each axial location. Within each genotype, measurements at each axial location were pooled to assess the variability in morphology along the length of the femur (FIG. 14). Qualitatively, there is greater variability between axial locations in the Brt1/+ bones (B) in comparison to the WT (A) bones.

All measurements within each bone were pooled to yield the mean fibril spacing for that bone (rightmost boxplot in each panel of FIG. 14, FIG. 15). Within each genotype, the overall mean values were 67.6 nm and 67.4 nm for WT and Brt1/+, respectively. There was no significant effect of genotype on mean fibril spacing (p=0.392) when the mean values from the 4 bones in each genotype were compared by One Way ANOVA.

In addition to mean differences in morphology, important information can also be obtained by viewing the population distribution of fibril morphologies within each genotype (FIG. 16). FIG. 16A shows that a distribution of spacings exists in each genotype and that these distributions differ between WT and dysplastic. The main population of fibrils in each group was defined using the mean of the WT group ±1 standard deviation, which is 66-70 nm (FIG. 16A). Within this range, 75% of WT, but only 55% of Brt1/+ fibrils, were found. As a second method to visualize these distributions, the Cumulative Distribution Function (CDF) was computed from the measurements in each group (FIG. 16B). Both the histogram and the CDF indicate that the Brt1/+ bones have a population of fibrils with closer spacing than does the WT group. To test for statistically significant differences between distributions, a fundamentally different comparison than the difference in means tested above using One Way ANOVA, Kolmogorov-Smirnov (K-S) tests were applied to the data. This test is sensitive to changes in both the mean value and standard deviation of a distribution. The population distribution of the D-periodic spacings in Brt1/+ bones was significantly different than the WT bones (p=0.001).

In these experiments, surface characterization of Type I collagen at the nanoscale was linked with biology in an effort to understand the ultrastructural mechanisms of an Osteogenesis Imperfecta (OI) phenotype in bone. Normal bone contains a distribution of Type I collagen fibril morphologies. As described herein, sheep subjected to two years of ovariectomy-induced estrogen depletion demonstrated a quantifiable change in this distribution as a function of the disease state. However, the direct effects of estrogen-depletion on collagen are unknown and it is therefore difficult to understand why this change in the distribution of fibril morphologies exists. A major strength of the present experiments is that a disease system with a well-defined genetic change in the col1α1 allele and a well characterized alteration in collagen protein structure was directly related to altered Type I collagen nanoscale morphology. By characterizing the mean fibril spacing and the distribution of fibril morphologies in the bone of normal mice and mice that were heterozygous for a specific col1α1 point mutation (G349C), phenotypic changes in the collagen fibril ultrastructure were detected.

Although the mean D-periodic spacing of Type I collagen fibrils in Brt1/+ bone was not significantly different than in WT, the distribution of spacing values was distinctive between the genotypes (FIG. 16). Further, there was more variation in fibril morphology along the axial length of Brt1/+ bones (FIG. 14). In light of what is known about the mutation in Brt1/+ mice and its detrimental effects on collagen synthesis, bone structure and overall bone mechanical integrity, these findings at the nanoscale are important. Bones from Brt1/+ mice have normal levels of col1α1 and col1α2 transcripts, and produce Type I collagen molecules with 3 different chain compositions molecules (2 normal α1 chains, +/+; 1 normal and 1 mutant α1 chain, G349C/+; 2 mutant α1 chains, G349C/G349C) in an expected 1:2:1 ratio. Abnormal trafficking of collagen molecules with a single mutant chain leads to the accumulation of collagen in the endoplasmic reticulum resulting in delayed secretion, over modification and selective degradation. As a result, among the total collagen molecules secreted from Brt1/+ cells, the proportion with a single mutant chain ranges from 26-40%, considerably lower than the theoretical 50%. Once mutant molecules are secreted from cells, they are efficiently incorporated into collagen fibrils and form crosslinks with the same efficiency as in WT mice.

Fibrils formed in Brt1/+ mice are thinner and exhibit a disruption of the normal quasi-crystalline lateral packing, but the methods used to measure these properties were indirect (N. V. Kuznetsova, A. Forlino, W. A. Cabral, J. C. Marini, S. Leikin, Structure, stability and interactions of type I collagen with GLY349-CYS substitution in alpha 1(I) chain in a murine Osteogenesis Imperfecta model, Matrix Biol. 23 (2004) 101-112.). Data from the current study directly demonstrate that the incorporation of mutant molecules changes the intrafibrillar organization of collagen fibrils. Changes in the D-period spacing are likely driven by alterations in the end-to end spacing of collagen molecules within the fibril due to changes in intracellular tropocollagen processing and assembly, or by a change in the tightness of the twist of the fibril. Since collagen forms the template for mineralization, altered collagen may also account for changes in mineral composition and density and may result in differences in the relationship between collagen and mineral. It is also possible that changes in the relationship between collagen, non-collagenous proteins and mineral are partially responsible for the observed changes in fibril morphology.

Recent modeling studies have investigated the effects of point mutations on collagen structure and mechanical integrity (A. Gautieri, S. Vesentini, F. M. Montevecchi, A. Redaelli, Mechanical properties of physiological and pathological models of collagen peptides investigated via steered molecular dynamics simulations, J. Biomech. 41 (2008) 3073-3077 and A. Gautieri, S. Uzel, S. Vesentini, A. Redaelli, M. J. Buehler, Molecular and mesoscale mechanisms of osteogenesis imperfecta disease in collagen fibrils, Biophys. J. 97 (2009) 857-865). In the first study, normal collagen helices and helices with single amino acid point mutations were modelled and the incorporation of these helices into triple helical collagen molecules was investigated. The major conclusion from this study was that the alteration of the normal amino acid sequence leads to packing differences in collagen molecules which could contribute to compromised mechanical integrity associated with OI. The current technology now directly observes that the alteration in amino acid sequence cause by a single point mutation in OI can lead to changes in fibril spacing. Further investigation showed that OI mutations can weaken intermolecular adhesions leading to decreased stiffness and failure strength of affected collagen fibrils. Interestingly, those investigators also reported an increase in intermolecular spacing, which would be expected to lead to an increase in the D-periodic spacing of the resulting fibril. In the current direct investigation of this phenomenon, mutant bone had a population of fibrils with decreased spacing although no change in the average fibril spacing was observed. An explanation for the disagreement between these observations is currently unknown. It is postulated that the decrease in fibril spacing that was observed in the current study means that less space is available inside of the fibril for water and mineral to occupy. The decrease in water will have a direct negative impact on the viscoelastic and post-yield behaviour of the fibril. Further, as mineral is no longer formed within the template that the fibrils provide, an increased proportion of extrafibrillar mineral will lead to the known hypermineralization phenotype that is characteristic of OI.

In sum, the nano scale morphology of Type I collagen was probed to gain a mechanistic understanding of changes induced in the collagen ultrastructure of bone in a murine model of Type IV Osteogenesis Imperfecta. Although the average D-periodic gap/overlap spacing in Brt1/+ bone was the same as WT, Brt1/+ bone shows greater variability of D-periodic spacing along the length of the bone and a significant difference in the population distribution of collagen fibrils. These observations at the nanoscale level provide insight into the structural basis for changes in bone composition, geometry and mechanical integrity in Brt1/+ bones. These changes in morphology may be directly related to alterations in nanoscale mechanical integrity.

The present technology further demonstrates that type I collagen nanoscale morphology is similar in male and female mice. From studies of inbred and congenic mouse strains and identification of quantitative trait loci (QTLs) responsible for bone composition, geometric and mechanical properties, it is known that the genetic control of bone is gender specific. Gender-specific responses to genetic deficiency and mechanical loading have also been demonstrated. Differences exist in musculoskeletal cells as a function of the gender of animal from which those cells were derived. The presence of these gender-specific skeletal phenotypes suggests that the efficacy of therapies designed to treat bone diseases may also be sex-specific.

Currently, little is known about gender-specific differences in bone extracellular matrix assembly and organization. Therefore, the present technology and experiments were designed to investigate sex-specific differences in the nanoscale morphology of Type I collagen in bone. It was hypothesized that differences would exist in the mean D-periodic axial gap/overlap spacing and population distributions of fibril morphologies as a function of gender in skeletally mature mice. However, the present study demonstrates that the average D-periodic gap/overlap spacing is not significantly different in male versus female bones within the ability of the present methods to detect a difference, and there is no difference in the distributions of these values. These nanoscale observations suggest that although differences exist in the cells derived from male and female animals, gender-specific differences in bone size, shape and mechanical integrity are likely derived at higher levels of the bone tissue hierarchy.

The following materials and methods were employed.

Mice from the C57BL/6J background strain were used with prior approval (University of Michigan, UCUCA protocol #09757). Four male mice and four female mice were sacrificed at 16 weeks of age by $CO_2$ inhalation. Both femora from each mouse were harvested, and stripped of soft tissue before use.

Atomic Force Microscopy (AFM) imaging and analysis included the following aspects. Before use, the proximal (above the third trochanter) and distal ends of each femur were removed using a low-speed sectioning saw. The marrow cavity of each bone was cleaned using a small tube brush. Bones were mounted, anterior-side up, to a steel disk using a thin layer of cyanoacrylate glue. A flat surface of intracortical bone was created using a 3 µm polycrystalline water-based diamond suspension and a polished finish was created a 0.05 µm deagglomerated alumina suspension (Buehler LTD; Lake Bluff, Ill.). Bones were sonicated for 15 seconds to remove polishing residue and debris. To remove extrafibrillar surface mineral and expose underlying collagen fibrils, each bone was demineralized using 0.5M EDTA at a pH of 8.0 for 15 minutes, then vigorously rinsed with ultrapure water and soaked at 4° C. for at least 16 hours. EDTA is often used in mineralized tissue research to remove mineral while keeping collagen and cells intact and viable. Before imaging, each sample was briefly sonicated to remove any mineral that was still bound to the surface.

Samples were imaged in air using a PicoPlus 5500 AFM (Agilent). Images were acquired in tapping mode using silicon cantilevers (VistaProbes T300R, tip radius<10 nm, force constant 40 N/m, resonance frequency 300 kHz; nanoScience Instruments; Phoenix, Ariz.) at line scan rates of 2 Hz or lower at 512 lines per frame. Making absolute x-y distance measurements with AFM has multiple limitations. Prior to sampling, calibration of the system was performed according manufacturer guidelines. This calibration led to a maximum tolerance of 1.1 nm.

Images were acquired from 9 axial locations in each bone sample (designated 1-9 beginning at the proximal end of the sample, FIG. 17). At each location, 3.5 µm×3.5 µm amplitude images were analyzed to investigate the D-periodic axial gap/overlap spacing, chosen as our key metric of fibril morphology (FIG. 12). Five to ten fibrils from each axial location were analyzed as previously described. Briefly, a rectangular region of interest (ROI) was chosen along straight segments of individual fibrils, starting and ending at the edge of a gap zone. A two dimensional Fast Fourier Transform (2D FFT) was performed and the primary peak from the 2D power spectrum was analyzed to determine the value of the D-periodic gap/overlap spacing. A detailed analysis of the uncertainty associated with this type of measurement sets the minimum bin size for population studies at 0.8 nm. For all histograms, the bin size was therefore set at 1 nm.

All statistical analyses utilized SPSS (Version 16.0, SPSS Inc.). For all investigations, a value of p<0.05 was considered significant. To investigate differences in fibril morphology within each gender as a function of axial location, the values at each location in each gender were pooled and compared using One Way ANOVA with post hoc Bonferroni tests. To investigate differences in fibril morphology as a function of gender, D-periodic axial spacing values measured from an individual sample were pooled, yielding an average value for that sample. The values from male (n=4) and female (n=4) mice were then compared using One Way ANOVA.

To examine differences in the distribution of fibril morphology between genotypes, histograms and the Cumulative Distribution Function (CDF) of each group were computed. The CDF shows the fraction of a given sample which is contained up to a particular value, easily demonstrating differences between distributions in both mean and standard deviation. To test for statistically significant differences between distributions, Kolmogorov-Smirnov (K-S) tests were applied to the data. This test is sensitive to changes in both the mean value and standard deviation of a distribution.

To quantitatively assess the nanoscale morphology of Type I collagen in murine cortical bone as a function of gender, femora from 16 week old male and female mice from the C57BL/6J background strain were used. In the intracortical bone along the anterior surface of the diaphysis, 9 axial locations were analyzed in 4 femora from each gender. At each axial location, 70 µm×70 µm scans were performed to find suitable sites for closer inspection (FIG. 17). The scan size was decreased to a final size of 3.5 µm×3.5 µm. At each axial location, 5-10 fibrils were analyzed. In total, 259 fibrils from male samples and 263 fibrils from female samples were analyzed.

By pooling data from the 4 bones in each gender at each of the 9 locations and analyzing the D-periodic spacing, it was confirmed that there were no systemic changes in Type I collagen morphology as a function of axial location in either gender (FIG. 18). The boxes represent the middle 50% of the data and the whiskers depict the data extremes. The diamond is the mean and the line within the box is the median of each group. The dashed horizontal line is for reference and corresponds to the 67 nm axial spacing that is predicted by the Hodge-Petruska model. Statistical comparisons were made between axial locations within each gender using One Way ANOVA with post hoc Bonferroni tests. Although some statistical differences did exist between locations in each gender (p<0.05; Male: 4 vs. 6; Female: 2 vs. 9, 2 vs. 5, 8 vs. 9), there were no systematic differences in either gender.

For each of the analyzed bones, the measurements within each bone were pooled to yield the mean fibril spacing for that bone. These mean values ranged from 67.3 nm to 68.9 nm in males and 67.5 and 69.5 nm in females, with an overall mean value from the 4 samples measured in each gender of 68.0 nm and 68.2 nm for males and females, respectively (FIG. 19). When the mean values in each group were compared by One Way ANOVA, no statistical differences were present between the genders.

FIG. 20a demonstrates that a distribution of fibril morphologies existed in bones from each gender. Qualitatively, there were no differences present in the male and female population distributions (n=259 fibrils in males, n=263 fibrils in females). As a second method to visualize the distributions, the Cumulative Distribution Function (CDF) was computed from the measurements in each group (FIG. 20b). A Kolmogorov-Smirnov (KS) test applied to the data indicates that the distributions from the male and female bones were statistically indistinguishable from one another (p=0.276).

The present technology demonstrates that in cortical bone of skeletally mature mice, there are no differences in the D-periodic gap/overlap spacing of Type I collagen as a function of gender within the ability of this method to detect a difference. The D-periodic spacing of Type I collagen was chosen as the metric to identify changes in nanoscale morphology because it is readily quantified and is derived from the structural arrangement of tropocollagen molecules within a collagen fibril (FIG. 12). The property is a fundamental characteristic of this ubiquitous structural protein and may be indicative of the state of the individual molecular triple helices, post-translational modifications and cross-linking. A previous study in male mice showed that a distribution of nanoscale morphologies (as measured by the D-periodic spacing) exists in Type I collagen-based tissues including bone, dentin and tendon. Further, collagen nanoscale morphology has been shown to differ as a function of disease in bone. Findings in this study suggest that although differences exist in the cells derived from male and female animals, gender is not a major factor that regulates this fundamental characteristic of Type I collagen in bone.

Serum sex steroids (most notably estradiol, progesterone and testosterone) are known to differ widely between male and female humans and mice, especially earlier in life. Notably, serum testosterone is roughly 20 times more abundant in males while basal estradiol and progesterone are elevated by 2-4 times in females. The current study suggests that these main hormonal differences between male and female mice may not play a role in regulating Type I collagen nanoscale morphology. However, as described herein, 2 years of estrogen depletion following ovariectomy (OVX) resulted in dramatic changes in collagen morphology in female sheep compared with sham operated control animals. In this case, the bones of these sheep developed under normal hormonal levels for 5 years. Following OVX in sheep, the production of female sex steroids are dramatically reduced but not completely abolished. Other metabolic changes may also be occurring following OVX. It seems probable that a combination of factors that are not completely understood are responsible for the changes noted in Type I collagen morphology.

At 16 weeks of age, mice are considered skeletally mature as most measures of bone formation (both dynamic markers and size parameters) have reached a steady state value, peak bone mass has been attained and mechanical integrity has leveled off near a maximum level. At this age, a mouse is roughly equivalent to a human in their middle twenties. Mice of this age were used to avoid the possible effects of rapid longitudinal and circumferential bone growth on collagen structure. At 16 weeks of age, C57BL/6J mice have well known gender-specific differences in bone size, shape and mechanical integrity. Therefore, the current study clearly indicates that in vivo, differences in Type I collagen structure are not responsible for gender differences in tissue quality or mechanical integrity in these mice.

In sum, these experiments show that the D-periodic gap/overlap spacing of Type I collagen is not impacted by gender, within the ability of the present technology and methods to detect a difference. This observation at the nanoscale suggests that although differences exist in the cells derived from male and female animals, gender-specific differences in bone size, shape and mechanical integrity are likely derived at higher organizational levels of the bone tissue hierarchy.

The present technology can be used in several ways. For example, the present methods can be used to overcome the limited prognostic capability of bone mineral density (BMD) analysis to diagnose subjects with bone diseases (e.g., osteoporosis) or can be used to detect bone diseases at an earlier time or stage (e.g., prior to the onset of clinical symptoms). The present methods can be used as screening and diagnostic methods.

In some embodiments, the methods described herein can determine whether a subject has a bone disease, such as for example, osteoporosis and osteogenesis imperfecta. Such methods can include the steps of: providing a bone sample from the subject; determining a collagen fibril morphology value of the bone sample; providing a reference value from a non-affected control subject, wherein the reference value is a collagen fibril morphology value from the same type of bone sample obtained from a population of non-affected control subjects; and comparing the collagen fibril morphology value of the bone sample to the reference value, wherein if the collagen fibril morphology value is altered versus the reference value, the subject is said to have a bone disease.

In some embodiments, bone of a subject can be diagnosed or screened to determine if the Type I collagen morphology is pathological and correlates to a collagen-related bone disease, for example, osteoporosis disease and osteogenesis imperfecta among others. Other bone diseases that may be diagnosed or analyzed also include diseases of the bone and joints or cartilage that involve defects in collagen formation or collagen structure. In some embodiments, the subject's bone disease and/or other collagenous related diseases of tendons, skin, cartilage, or joints can be diagnosed and/or analyzed using cartilage samples from tendons, skin, joints, and other collagen structures using biopsy procedures.

In some embodiments, the present methods can be employed by first providing a bone sample from the subject. The bone sample can be obtained from the subject via biopsy or following a surgical procedure (e.g. joint replacement, dental extraction and the like). AFM can also be performed on live subjects by preparing a sample of tissue and exposing the subject's bone sample for further study. As used herein, a bone sample can include any cortical or trabecular bone and parts thereof including the diaphysis, metaphysic, and epiphysis portions of the bone. In some embodiments, the bone sample can include part or the whole tooth surface of one or more teeth, either extracted or in situ in the mouth of the subject. For diagnosing and screening infants and young children, deciduous teeth fall out during child hood can be used as a bone sample in the methods described herein.

In some embodiments, an extracted portion of bone can be removed from the subject in order to determine a collagen fibril morphology value using AFM and 2-dimensional fast Fourier transformation (2D-FFT) to derive the collagen fibril spacing data obtained from the AFM images of collagen. In still other embodiments, a collagen fibril morphology value can be determined using AFM and 2D-FFT on the surface of one or more teeth, in a non-invasive manner. Likewise, in some embodiments a collagen fibril morphology value can be determined using a subject's skin. The skin may be from a biopsy or may be analyzed directly on the subject.

In some embodiments, the collagen fibril morphology value is a physiological feature of the subject's arrangement of type I, II, III or IV collagen in the subject's bone sample. It has been unexpectedly and surprisingly found that the collagen fibrils contained on or within bone can be used to determine whether the subject has a bone disease, as described above, for example, osteoporosis and osteogenesis imperfecta, by determining the spacing and distribution of the fibrils imaged using AFM and calculated using 2D-FFT. For each determination of the collagen fibril morphology value, for example, the fibril spacing and the distribution of fibril spacing within a given bone sample, a 2D-FFT can be performed on a flat plane surface of a bone sample. The 2D power spectrum derived from the 2D-FFT can be analyzed to determine the value of the D-periodic gap/overlap spacing, which is an example of a collagen fibril morphology value. The 2D-FFT analysis can yield data for all angular orientations and a sampling size of 9 D-period repeats, for example, can be used to determine the fibril spacings. The method can alternatively include determining the variability in the fibril spacings as a second illustrative example of a collagen fibril morphology value. Multiple analyzed sections of a given bone can provide a mean fibril spacing for that bone; e.g., a tooth, tibia or femur.

In some embodiments, the method compares the subject's mean fibril spacing for that tissue sample or type of bone and the variability of the fibril spacings determined by multiple measurements and compares to a population of mean fibril spacings for the same type of tissue or bone in subjects that are medically verified as not having the bone disease of interest. The reference value can be any quantitative collagen fibril morphology value, including as illustrative examples, mean fibril spacing and fibril spacing variance for a given bone sample. Reference values can be determined in the exact same way as the subject's mean fibril spacing since AFM is a non-invasive technique and when combined with 2D-FFT for calculating the collagen fibril morphology value for the control group not afflicted with the bone disease can be used to determine the reference value.

In some embodiments of the present disclosure, the mean fibril spacing and/or variation on fibril spacing can be used as a collagen fibril morphology value to diagnose a subject with osteoporosis and other bone diseases or used as a basis for screening subjects that wish to know whether they are in fact suffering from disease. It has been unexpectedly found that bones in two diseases, osteoporosis and osteogenesis imperfecta, have a significant impact on the distribution of fibril morphology that may indicate flaws in the collagen fibrils from misalignment or over-modification, changes that can be compensated for over larger length scales. Other characteristics such as variability in the mean fibril spacing and fibril spacing themselves can be ready extrapolated from the AFM and 2D-FFT analysis of the subject's bone sample and correlate the experimentally determined collagen fibril morphology value with those of reference values for the same bone sample in healthy controls. If the subject's mean fibril spacing is altered compared with the reference value or if the distribution of fibrils is altered in comparison to a reference distribution value, then the subject can be presumptively diagnosed as having a bone disease and can be confirmed with mineral density tests, for example.

In still other embodiments, diseases of the joint, tendons, skin, spine and other collagen related structures can also be diagnosed, analyzed and studied using the subject's mean fibril spacing and distribution pattern from collagenous tissue. If the subject's mean fibril spacing and distribution pattern is altered compared with the reference value or if the distribution of fibrils is altered in comparison to a reference distribution value, the subject is presumptively diagnosed with a disease of the joint, cartilage or spine, for example. In some embodiments, the distribution in the mean fibril spacing when compared to a reference value serves as a good diagnostic collagen fibril morphology value for the presence of a collagen related disease. For example, the large increase in the smaller D-spacing is a good indicator of a bone disease. In other words, a large fraction of the population shifting to lower values is correlated to the presence of a bone disease, for example, osteoporosis and osteogenesis imperfecta.

In some embodiments, methods for identifying a subject as a disease candidate (the disease affecting tissue comprising collagen) include using scanning electron microscopy in place of atomic force microscopy, as described herein. For example, determining a collagen fibril morphology value of the tissue sample can include imaging the tissue using scanning electron microscopy. D-periodic gap/overlap spacing of a collagen fibril can then be measured to provide the collagen fibril morphology value. The reference value can include a D-periodic gap/overlap spacing of a collagen fibril from the control subject. In some cases, measuring D-periodic gap/overlap spacing of a collagen fibril to provide the collagen fibril morphology value further comprises measuring D-periodic gap/overlap spacing of a plurality of collagen fibrils to provide the collagen fibril morphology value. Likewise, the reference value can further comprise a D-periodic gap/overlap spacing of a plurality of collagen fibrils from the control subject. Comparing the collagen fibril morphology value of the tissue sample to the reference value can then including comparing at least one of an overall mean and a distribution of the D-periodic gap/overlap spacing of the plurality of collagen fibrils.

Imaging using scanning electron microscopy can be performed as known in the art. For example, a specimen typically needs to be dry as the specimen chamber is at high vacuum. Hard and dry materials can be prepared relatively easily from collagenous tissues such as bone or dentin, which can be imaged with little further treatment. However, living cells and soft collagenous tissues, such as tendon and skin can require chemical fixation to preserve and stabilize their structure. Fixation, for example, can be performed by incubation in a solution of a chemical fixative (e.g., glutaraldehyde, formaldehyde, among others) and can include a postfixation treatment with osmium tetroxide. Fixed tissue can then be dehydrated while trying to maintain structure. Because air-drying can result in collapse and shrinkage, it is commonly achieved by critical point drying, where water in the cells is replaced with organic solvents such as ethanol or acetone, and replacement of these solvents in turn with a transitional fluid such as liquid carbon dioxide at high pressure. In the case of liquid carbon dioxide, the carbon dioxide can be removed while in a supercritical state, so that no gas-liquid interface is present within the sample during drying. The dry specimen can then be mounted using an adhesive, such as epoxy resin or electrically-conductive double-sided adhesive tape, and sputter coated with a metal such as gold or gold/palladium alloy before imaging in the microscope.

Sputter coating can be performed with a metal such as gold. Gold has a high atomic number and sputter coating with gold produces high topographic contrast and resolution. However, the coating has a thickness of a few nanometers, and can obscure underlying fine detail of a specimen at very high magnification. Low-vacuum scanning electron microscopes with differential pumping apertures allow samples to be imaged without such coatings and without the loss of natural contrast caused by the coating, but may not achieve the resolution attainable by conventional scanning electron microscopes with coated specimens.

When using a scanning electron microscope equipped with a cold stage for cryo-microscopy, cryofixation may be used and low-temperature scanning electron microscopy performed on cryogenically-fixed tissue comprising collagen. Cryo-fixed tissue may be cryo-fractured under vacuum to reveal internal structure, sputter coated, and transferred onto the scanning electron microscope cryo-stage while still frozen. For example, freeze-fracturing, freeze-etch, or freeze-and-break preparation methods are available.

The following definitions and non-limiting guidelines should be considered in reviewing the description of the technology set forth herein. The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "desire" or "desirable" refer to embodiments of the technology that afford certain benefits, under certain circumstances. However, other embodiments may also be desirable, under the same or other circumstances. Furthermore, the recitation of one or more desired embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters.

When an element or layer is referred to as being "on," "engaged to," "connected to" or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

What is claimed is:

1. A method for identifying a subject as a disease candidate, the disease affecting tissue comprising collagen, the method comprising:
   providing a tissue sample from the subject, wherein the tissue comprises collagen;
   determining a collagen fibril morphology value of the tissue sample;
   providing a reference value, wherein the reference value comprises a reference collagen fibril morphology value determined using a tissue sample from a control subject, wherein the tissue sample from the control subject is the same type of tissue as the tissue sample from the subject;
   comparing the collagen fibril morphology value of the tissue sample to the reference value; and identifying the subject as a disease candidate when the collagen fibril morphology value is different from the reference value,
wherein determining the collagen fibril morphology value of the tissue sample comprises
  imaging the tissue; and
  measuring D-periodic gap/overlap spacing of a plurality of collagen fibrils to provide the collagen fibril morphology value;
  wherein measuring D-periodic gap/overlap spacing of a plurality of collagen fibrils to provide the collagen fibril morphology value comprises performing a two-dimensional Fast Fourier Transform for each fibril and analyzing the primary peak from a resulting two-dimensional power spectrum to determine the D-periodic gap/overlap spacing value.

2. The method of claim 1, wherein the tissue sample comprises dentin, bone, tendon, or skin.

3. The method of claim 1, wherein the tissue comprises type I collagen.

4. The method of claim 1, wherein providing a tissue sample from the subject comprises taking a biopsy of the tissue from the subject.

5. The method of claim 1, wherein the tissue sample is demineralized using ethylenediaminetetraacetic acid.

6. The method of claim 1, comprising
  imaging the tissue using atomic force microscopy.

7. The method of claim 1, wherein the reference value comprises a D-periodic gap/overlap spacing of a plurality of collagen fibrils from the control subject.

8. The method of claim 1, wherein the collagen fibril morphology value is at least one of an overall mean and a distribution of the D-periodic gap/overlap spacing of the plurality of collagen fibrils.

9. The method of claim 6, wherein imaging the tissue using atomic force microscopy is performed in tapping mode.

10. The method of claim 1, comprising:
  imaging the tissue using scanning electron microscopy.

11. The method of claim 1, wherein the subject and the control subject are not the same sex.

12. The method of claim 1, wherein the reference value comprises a reference collagen fibril morphology value determined using a plurality of tissue samples from a plurality of control subjects.

13. The method of claim 12, wherein the plurality of control subjects includes a male control subject and a female control subject.

14. The method of claim 1, wherein the tissue sample comprises bone tissue and the disease comprises osteoporosis.

15. The method of claim 14, wherein:
determining a collagen fibril morphology value of the tissue sample comprises:
  imaging the tissue using atomic force microscopy; and
  measuring D-periodic gap/overlap spacing of a plurality of collagen fibrils to provide the collagen fibril morphology value, and the reference value comprises a D-periodic gap/overlap spacing of a plurality of collagen fibrils from the control subject; and
identifying the subject as a disease candidate when the collagen fibril morphology value is different from the reference value comprises:
  identifying the subject as an osteoporosis candidate when an overall mean or a distribution of the D-periodic gap/overlap spacing of the plurality of collagen fibrils for the subject is different than the reference value from the control subject.

16. The method of claim 1, wherein the tissue sample comprises bone tissue and the disease comprises osteogenesis imperfecta.

17. The method of claim 16, wherein:
determining a collagen fibril morphology value of the tissue sample comprises:
  imaging the tissue using atomic force microscopy; and
  measuring D-periodic gap/overlap spacing of a plurality of collagen fibrils to provide the collagen fibril morphology value, and the reference value comprises a D-periodic gap/overlap spacing of a plurality of collagen fibrils from the control subject; and
identifying the subject as a disease candidate when the collagen fibril morphology value is different from the reference value comprises:
  identifying the subject as an osteogenesis imperfecta candidate when the D-periodic gap/overlap spacing shows a greater variability along the length of the bone than the reference value from the control subject; or
  identifying the subject as an osteogenesis imperfecta candidate when the D-periodic gap/overlap spacing shows a difference in the population distribution of collagen fibrils compared to the reference value from control subject.

18. A method of diagnosing an individual as having or not having a disease or condition affecting collagen by determining a morphology value for collagen in the individual and comparing the morphology value to that of a control subject, the method comprising determining the morphology value with a method comprising:
  providing a tissue sample from the subject, wherein the tissue comprises collagen; and
  determining a collagen fibril morphology value of the tissue sample;
wherein determining the collagen fibril morphology value of the tissue sample comprises
  imaging the tissue; and
  measuring D-periodic gap/overlap spacing of a plurality of collagen fibrils to provide the collagen fibril morphology value;
  wherein measuring D-periodic gap/overlap spacing of a plurality of collagen fibrils to provide the collagen fibril morphology value comprises performing a two-dimensional Fast Fourier Transform for each fibril and analyzing the primary peak from a resulting two-dimensional power spectrum to determine the D-periodic gap/overlap spacing value.

* * * * *

UNITED STATES PATENT AND TRADEMARK OFFICE
CERTIFICATE OF CORRECTION

PATENT NO.        : 8,568,692 B2
APPLICATION NO.   : 12/847408
DATED             : October 29, 2013
INVENTOR(S)       : Banaszak-Holl et al.

It is certified that error appears in the above-identified patent and that said Letters Patent is hereby corrected as shown below:

In the Specification

Column 2, line 32, delete "1" and insert --I--.

Column 5, line 23, delete "Brt1/+" and insert --Brtl/+--.

Column 5, line 30, delete "Brt1/+" and insert --Brtl/+--.

Column 5, line 37, delete "Brt1/+" and insert --Brtl/+--.

Column 5, line 42, delete "Brt1/+" and insert --Brtl/+--.

Column 5, line 48, delete "Brt1/+" and insert --Brtl/+--.

Column 7, line 55, delete "(BH1/+)" and insert --(Brtl/+)--.

Column 7, line 60, delete "Brt1/+" and insert --Brtl/+--.

Column 7, line 63, delete "Brt1/+" and insert --Brtl/+--.

Column 7, line 66, delete "Brt1/+" and insert --Brtl/+--.

Column 8, line 2, delete "Brt1/+" and insert --Brtl/+--.

Column 8, line 59, delete "C M," and insert --C. M.,--.

Column 8, line 59, delete "C A," and insert --C. A.,--.

Column 8, line 60, delete "J L," and insert --J. L.,--.

Column 8, line 66, delete "down)," and insert --down).--.

Column 9, line 2, delete "LTD;" and insert --Ltd.,--.

Signed and Sealed this
Tenth Day of March, 2015

Michelle K. Lee
*Deputy Director of the United States Patent and Trademark Office*

Column 9, line 11, delete "R," and insert --R.,--.

Column 9, line 11, delete "A," and insert --A.,--.

Column 9, line 13, delete "1986:" and insert --1986;--.

Column 9, line 14, delete "J," and insert --J.,--.

Column 9, line 14, delete "E H," and insert --E. H.,--.

Column 9, line 14, delete "C M," and insert --C. M.,--.

Column 9, line 15, delete "L G," and insert --L. G.,--.

Column 9, line 15, delete "C" and insert --C.--.

Column 9, line 21, delete "in fibrillar" and insert --intrafibrillar--.

Column 9, line 21, delete "M," and insert --M.,--.

Column 9, line 21, delete "S," and insert --S.,--.

Column 9, line 22, delete "J H," and insert --J. H.,--.

Column 9, line 22, delete "S J," and insert --S. J.,--.

Column 9, line 22, delete "G" and insert --G.,--.

Column 10, line 7, delete "16.0." and insert --16.0,--.

Column 10, line 49, delete "A J," and insert --A. J.,--.

Column 10, line 49, delete "J" and insert --J.--.

Column 10, line 51, delete "G N," and insert --G. N.,--.

Column 10, line 52, delete "York;" and insert --York:--.

Column 11, line 9, delete "(p=0.048)," and insert --(p=0.048).--.

Column 11, line 36, delete "S," and insert --S.,--.

Column 11, line 36, delete "M," and insert --M.,--.

Column 11, line 37, delete "S J," and insert --S. J.,--.

Column 11, line 37, delete "G," and insert --G.,--.

Column 11, line 37, delete "G W," and insert --G. W.,--.

Column 12, line 22, delete "S," and insert --S.,--.

CERTIFICATE OF CORRECTION (continued)
U.S. Pat. No. 8,568,692 B2

Column 12, line 22, delete "M," and insert --M.,--.

Column 12, line 22, delete "S J," and insert --S. J.,--.

Column 12, line 22, delete "G," and insert --G.,--.

Column 12, line 22, delete "G" and insert --G.--.

Column 12, line 37, after "specialized", insert --,--.

Column 13, line 16, delete "vacuum in" and insert --vacuum. In--.

Column 13, line 25, delete "extrafibrilla" and insert --extrafibrillar--.

Column 13, line 26, delete "J H," and insert --J. H.,--.

Column 13, line 26, delete "P J," and insert --P. J.,--.

Column 13, line 26, delete "M E," and insert --M. E.,--.

Column 13, line 41, delete "minimal," and insert --minimal.--.

Column 14, line 2, delete "serving as" and insert --as serving--.

Column 15, line 19, delete "LTD;" and insert --Ltd.,--.

Column 19, line 63, delete "Brt1" and insert --Brtl--.

Column 20, line 28, delete "(Brt1)" and insert --(Brtl)--.

Column 20, line 52, delete "(Brt1/+)" and insert --(Brtl/+)--.

Column 20, line 58, delete "Brt1/+" and insert --Brtl/+--.

Column 20, line 60, delete "Brt1/+" and insert --Brtl/+--.

Column 20, line 61, delete "Brt1/+" and insert --Brtl/+--.

Column 20, line 64, delete "Brt1/+" and insert --Brtl/+--.

Column 20, line 67, delete "Brt1/+" and insert --Brtl/+--.

Column 21, line 2, delete "Brt1/+" and insert --Brtl/+--.

Column 21, line 6, delete "Brt1/+" and insert --Brtl/+--.

Column 21, line 8, after "imaging", insert --.--.

Column 21, line 18, delete "LTD;" and insert --Ltd.,--.

Column 22, line 12, delete "Brt1/+" and insert --Brtl/+--.

CERTIFICATE OF CORRECTION (continued)

Column 22, line 38, delete "Brt1/+" and insert --Brtl/+--.

Column 22, line 44, delete "Brt1/+" and insert --Brtl/+--.

Column 22, line 56, delete "Brt1/+" and insert --Brtl/+--.

Column 22, line 60, delete "Brt1/+" and insert --Brtl/+--.

Column 23, line 1, delete "Brt1/+" and insert --Brtl/+--.

Column 23, line 24, delete "Brt1/+" and insert --Brtl/+--.

Column 23, line 27, delete "Brt1/+" and insert --Brtl/+--.

Column 23, line 29, delete "Brt1/+" and insert --Brtl/+--.

Column 23, line 32, delete "Brt1/+" and insert --Brtl/+--.

Column 23, line 41, delete "Brt1/+" and insert --Brtl/+--.

Column 23, line 47, delete "Brt1/+" and insert --Brtl/+--.

Column 24, line 39, delete "nano scale" and insert --nanoscale--.

Column 24, line 43, delete "Brt1/+" and insert --Brtl/+--.

Column 24, line 44, delete "Brt1/+" and insert --Brtl/+--.

Column 24, line 49, delete "Brt1/+" and insert --Brtl/+--.

Column 25, line 33, delete "LTD;" and insert --Ltd.,--.

In the Claims

Column 33, claim 1, line 5, after "comprises", insert --:--.

Column 33, claim 6, line 26, after "comprising", insert --:--.

Column 34, claim 18, line 45, after "comprises", insert --:--.